(12) United States Patent
Gourley

(10) Patent No.: US 9,063,117 B2
(45) Date of Patent: Jun. 23, 2015

(54) MICRO-OPTICAL CAVITY WITH FLUIDIC TRANSPORT CHIP FOR BIOPARTICLE ANALYSIS

(76) Inventor: Paul L. Gourley, Albuquerque, NM (US)

( * ) Notice: Subject to any disclaimer, the term of this patent is extended or adjusted under 35 U.S.C. 154(b) by 619 days.

(21) Appl. No.: 13/337,051

(22) Filed: Dec. 24, 2011

(65) Prior Publication Data

US 2015/0049333 A1 Feb. 19, 2015

Related U.S. Application Data

(63) Continuation-in-part of application No. 12/034,640, filed on Feb. 20, 2008, now Pat. No. 8,209,128.

(60) Provisional application No. 60/902,685, filed on Feb. 21, 2007.

(51) Int. Cl.
- *G01N 33/48* (2006.01)
- *G01N 33/483* (2006.01)
- *G01N 15/14* (2006.01)

(52) U.S. Cl.
CPC ........ *G01N 33/4833* (2013.01); *G01N 15/1484* (2013.01); *G01N 15/1404* (2013.01); *G01N 2015/1493* (2013.01)

(58) Field of Classification Search
CPC ................ G01N 33/574; G01N 21/47; G01N 2015/1493; G01N 15/1429; G01N 21/6428; G01N 21/7746
USPC ..................... 702/19; 356/154, 246, 454, 318; 372/39, 70, 50.1, 61, 101; 422/82.08
See application file for complete search history.

(56) References Cited

U.S. PATENT DOCUMENTS

| | | | | |
|---|---|---|---|---|
| 5,065,407 A | * | 11/1991 | Pax | 372/103 |
| 5,596,401 A | | 1/1997 | Kusuzawa | |
| 5,608,519 A | * | 3/1997 | Gourley et al. | 356/318 |

(Continued)

FOREIGN PATENT DOCUMENTS

| | | |
|---|---|---|
| JP | 2002019268 A | 1/2002 |
| JP | 2005091467 A | 4/2005 |

OTHER PUBLICATIONS

Born, M. and E. Wolf, Principles of Optics, (Pergamon, Oxford, 1980), chapter 7.

(Continued)

*Primary Examiner* — Carol S Tsai

(57) ABSTRACT

This invention provides new methods and apparatus for rapidly analyzing single bioparticles to assess their material condition and health status. The methods are enabled by a resonant cavity to measure optical properties related to the bioparticle size and refractive index. Refractive index measurements are useful for determining material properties and biomolecular composition of the bioparticle. These properties and composition are dependent on the health state of the bioparticle. Thus, measured optical properties can be used to differentiate normal (healthy) and abnormal (diseased) states of bioparticles derived from cells or tissues. The methods are illustrated with data obtained from a resonator with a gain medium. The invention also provides new methods for multiple measurements in a single device, analyzing and manipulating bioparticles that are much smaller than the wavelength of light, and provides a microfluidic transport chip to enable rapid single bioparticle analysis of large populations of bioparticles.

26 Claims, 17 Drawing Sheets

(56) References Cited

U.S. PATENT DOCUMENTS

| | | | |
|---|---|---|---|
| 5,793,485 A * | 8/1998 | Gourley | 356/318 |
| 5,920,390 A | 7/1999 | Farahi | |
| H1911 H * | 11/2000 | Land | 264/1.36 |
| 6,187,592 B1 | 2/2001 | Gourley | |
| 6,421,364 B2 * | 7/2002 | Lubrano | 372/61 |
| 6,434,180 B1 * | 8/2002 | Cunningham | 372/50.1 |
| 6,454,945 B1 | 9/2002 | Weigl | |
| 6,658,037 B2 * | 12/2003 | Kahen et al. | 372/70 |
| 6,668,111 B2 | 12/2003 | Tapalian | |
| 6,833,542 B2 | 12/2004 | Wang | |
| 6,879,618 B2 * | 4/2005 | Cok et al. | 372/70 |
| 6,884,624 B1 | 4/2005 | Gourley | |
| 6,970,488 B2 * | 11/2005 | Spoonhower et al. | 372/39 |
| 6,975,400 B2 | 12/2005 | Ortyn | |
| 6,999,170 B2 | 2/2006 | Takeuchi | |
| 7,012,696 B2 * | 3/2006 | Orr et al. | 356/454 |
| 7,029,631 B2 * | 4/2006 | Leonard et al. | 422/82.08 |
| 7,050,613 B2 | 5/2006 | Murao | |
| 7,095,010 B2 | 8/2006 | Scherer | |
| 7,122,384 B2 | 10/2006 | Prober | |
| 7,149,396 B2 | 12/2006 | Schmidt | |
| 7,149,561 B2 | 12/2006 | Diab | |
| 7,177,018 B2 * | 2/2007 | Seeley | 356/154 |
| 7,187,441 B1 | 3/2007 | Sevick-Muraca | |
| 7,257,279 B2 | 8/2007 | Guo | |
| 7,279,883 B2 | 10/2007 | Sohn | |
| 7,294,503 B2 | 11/2007 | Quake | |
| 7,298,478 B2 | 11/2007 | Gilbert | |
| 7,393,699 B2 | 7/2008 | Tran | |
| 7,504,665 B2 * | 3/2009 | Summers | 257/82 |
| 7,573,921 B2 | 8/2009 | Yumoto | |
| 7,733,497 B2 | 6/2010 | Yun | |
| 7,970,041 B2 * | 6/2011 | Arimoto et al. | 372/101 |
| 8,176,630 B2 * | 5/2012 | Kataoka et al. | 29/890.1 |
| 8,209,128 B1 * | 6/2012 | Gourley | 702/19 |
| 8,266,791 B2 * | 9/2012 | Borenstein et al. | 29/830 |
| 8,797,527 B2 * | 8/2014 | Hukari et al. | 356/246 |
| 2003/0189711 A1 * | 10/2003 | Orr et al. | 356/484 |
| 2004/0004988 A1 * | 1/2004 | Cok et al. | 372/70 |
| 2004/0076198 A1 * | 4/2004 | Spoonhower et al. | 372/20 |
| 2004/0118599 A1 * | 6/2004 | Chason et al. | 174/260 |
| 2005/0118731 A1 | 6/2005 | Salafsky | |
| 2005/0201425 A1 | 9/2005 | Yakymyshyn et al. | |
| 2006/0138434 A1 * | 6/2006 | Summers | 257/84 |
| 2007/0086918 A1 * | 4/2007 | Hartley et al. | 422/73 |
| 2007/0269901 A1 | 11/2007 | Armani et al. | |
| 2007/0285843 A1 | 12/2007 | Tran | |
| 2008/0181828 A1 | 7/2008 | Kluck | |
| 2008/0186503 A1 * | 8/2008 | Kiesel et al. | 356/454 |
| 2008/0247436 A1 * | 10/2008 | Carter et al. | 372/50.11 |
| 2009/0014394 A1 * | 1/2009 | Yi et al. | 210/767 |
| 2009/0214755 A1 | 8/2009 | Armani et al. | |
| 2009/0268772 A1 * | 10/2009 | Arimoto et al. | 372/50.23 |
| 2011/0126617 A1 * | 6/2011 | Bengoechea Apezteguia et al. | 73/146 |

OTHER PUBLICATIONS

Gourley et al., "Semiconductor Microcavity Laser Spectroscopy . . . ," SPIE Conf. pub. 4265, Photonics West 4265, 113-125 (2001).

Gourley, et al. "Nano-squeezed light . . . ," SPIE Conf. pub 5345, Photonics West, Jan. 26-27, 2004, San Jose, CA, p. 51-60.

Gourley, et al., "Biomolecular Divergence . . . ," J. BioMedical Optics 12, p. 054003-1 to 14, (2007).

Gourley, et al., "Biocavity Laser Spectroscopy . . . ," SPIE Conf, San Jose, CA, Jan. 23-25, (2006).

Gourley, et al., "Optical Phenotyping . . . ," IEEE J. of Selected Topics in Quantum Electron. 11, Jul./Aug. 2005, p. 818-826.

Gourley, et al. "Brief Overview of BioMicroNano Technologies," Biotechnololgy Progress 21, 2-10 (2005).

Beauvoit, T. Kitai, and B. Chance, "Contribution of the mitochondrial compartment to the optical properties of the rat liver: a theoretical and practical approach.," Biophys J. 67(6), 2501-2510. (1994).

Karu, T. I., L. V. Pyatibrat, S. F. Kolyakov, N. I. Afanasyeva, "Absorption measurements of a cell monolayer relevant to phototherapy: Reduction of cytochrome c oxidase under near IR radiation," Journal of Photochemistry and Photobiology B: Biology 81, 98-106 (2005).

Barer, R. "Refractometry and Interferometry of Living Cells," J. Opt. Soc. Am. 47, pp. 545-552. (1957).

Landau, L. D. and E. M. Lifshitz, Statistical Physics, 2 ed. (Pergamon Press, New York, 1970), pp. 277-279.

Lindgren, B., Statistical Theory, 4th ed. (Chapman and Hall/CRC, Boca Raton, 1993).

Gourley, "Biocavity Laser for High-Speed Cell and Tumor Biology," J. Phys. D: Appl. Phys. 36 (14) R228-R239 (2003).

* cited by examiner

TOP VIEW

ΔL

L

REFLECTING SURFACES

SIDE VIEW

56 GRADED CAVITY

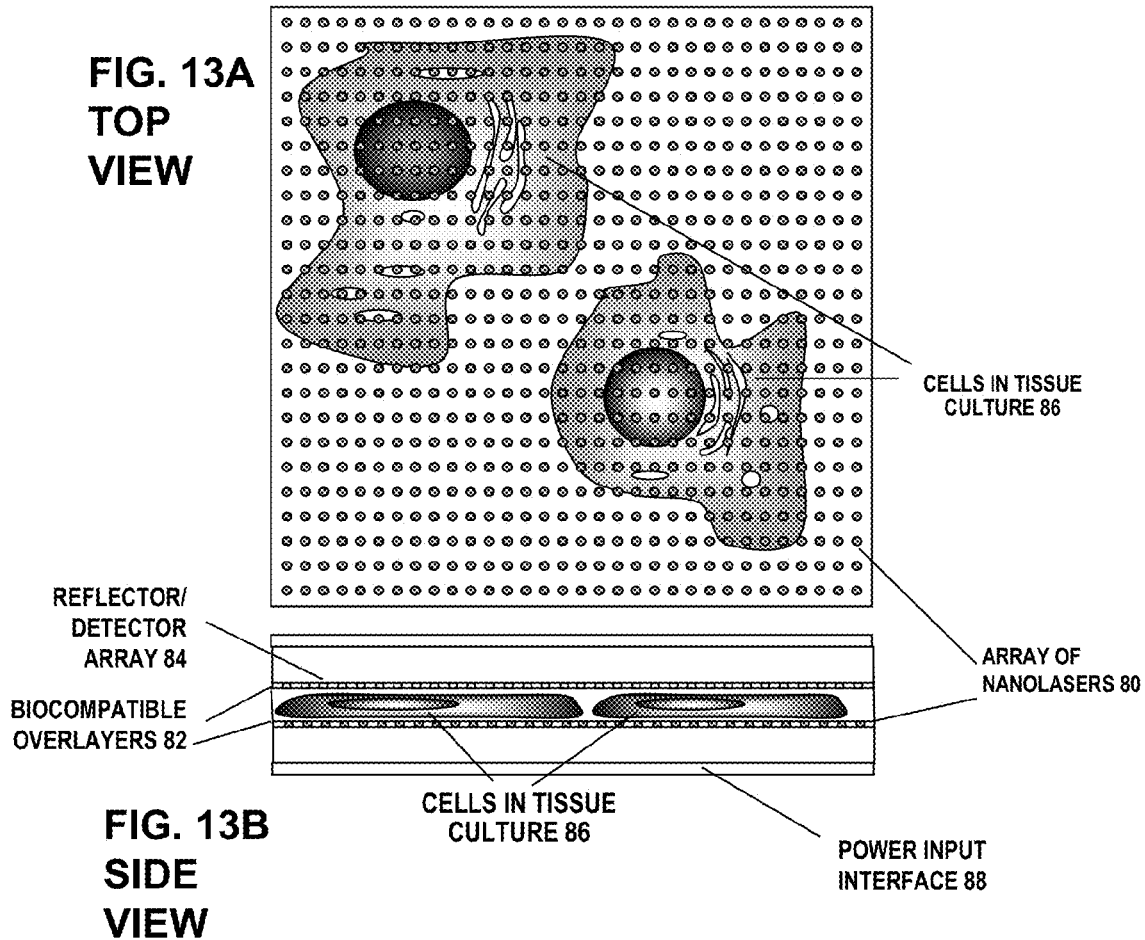

View into recessed surface

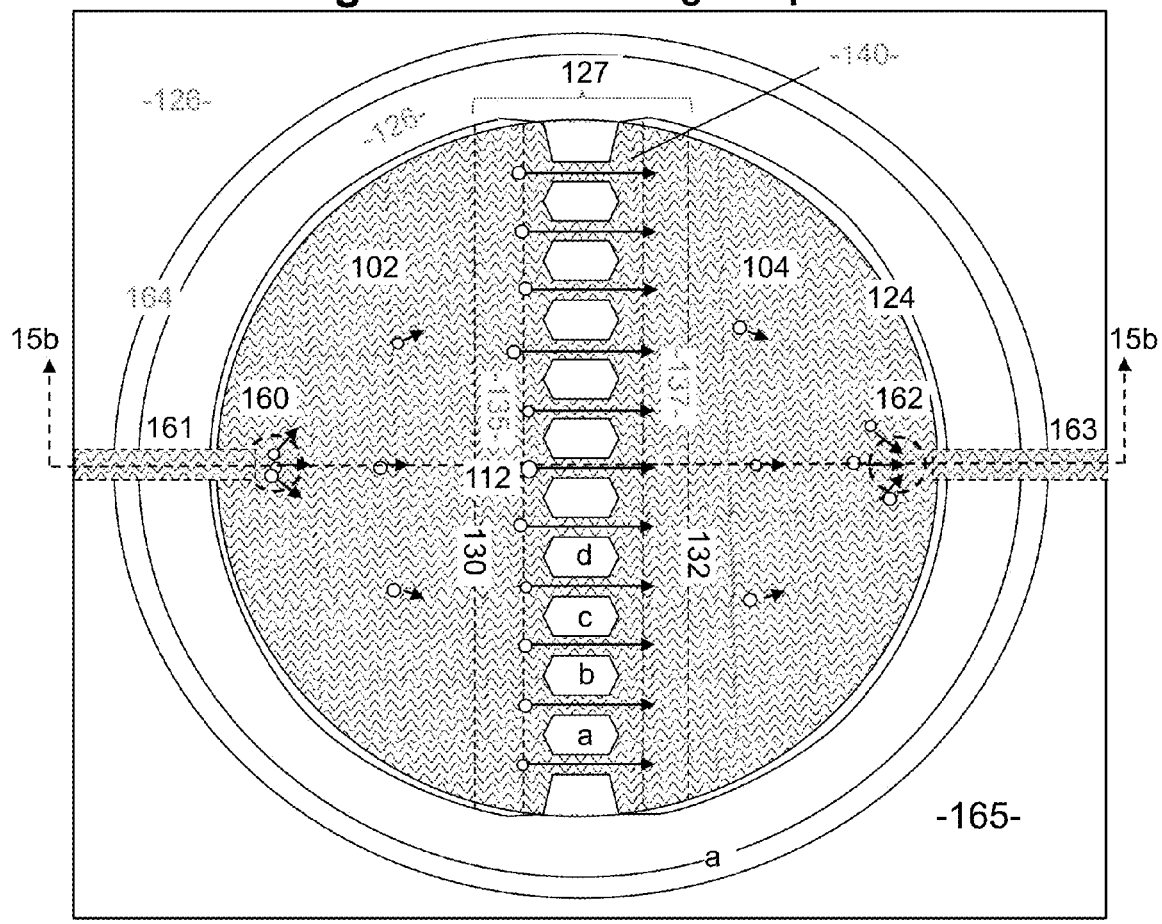
Fig. 15A view through chip surface -165-
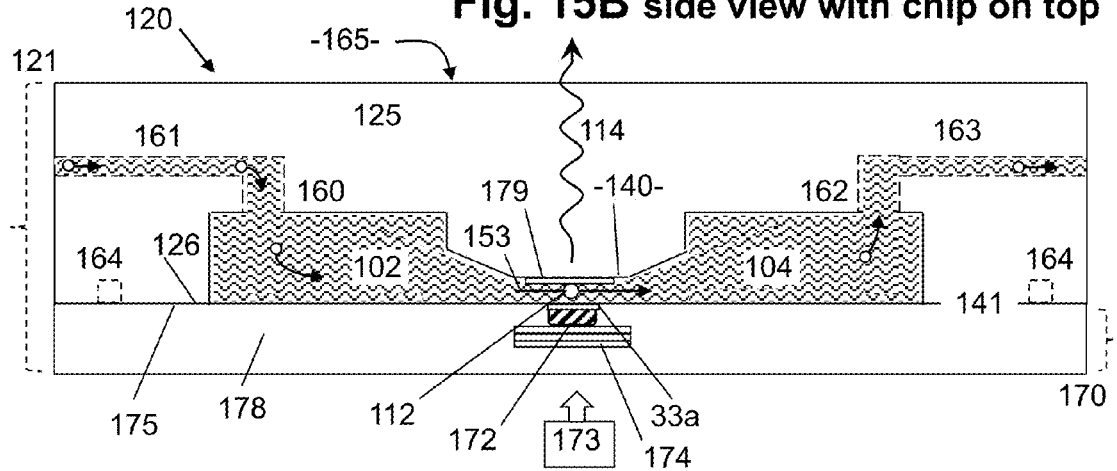
Fig. 15B side view with chip on top

Fig. 16A view through chip surface -165-
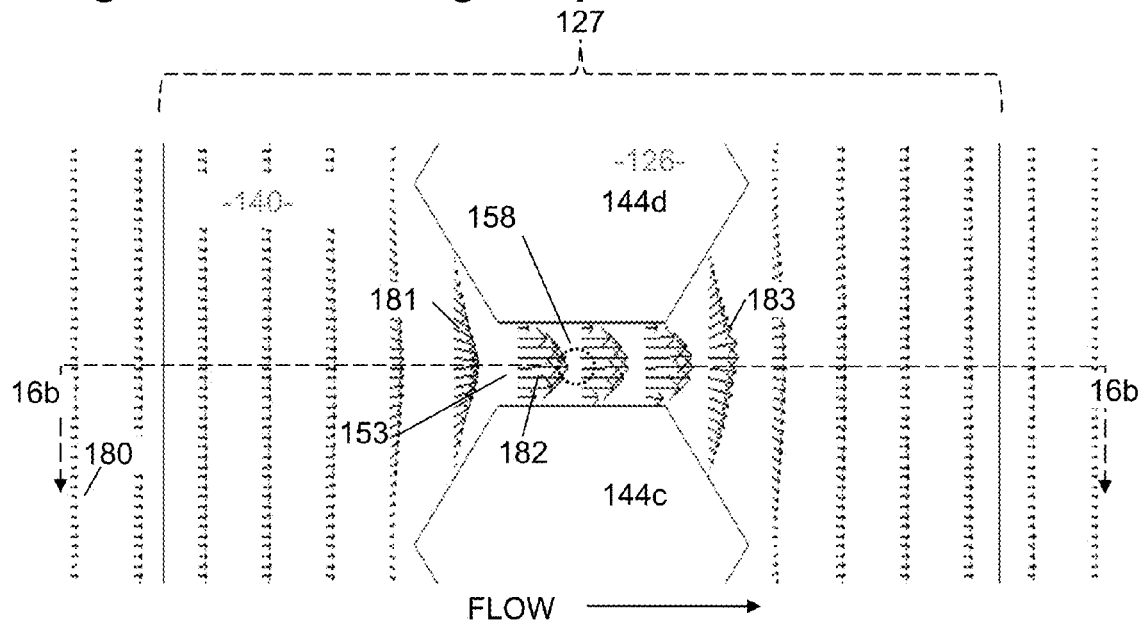
FLOW →
Fig. 16B side view with cover at top
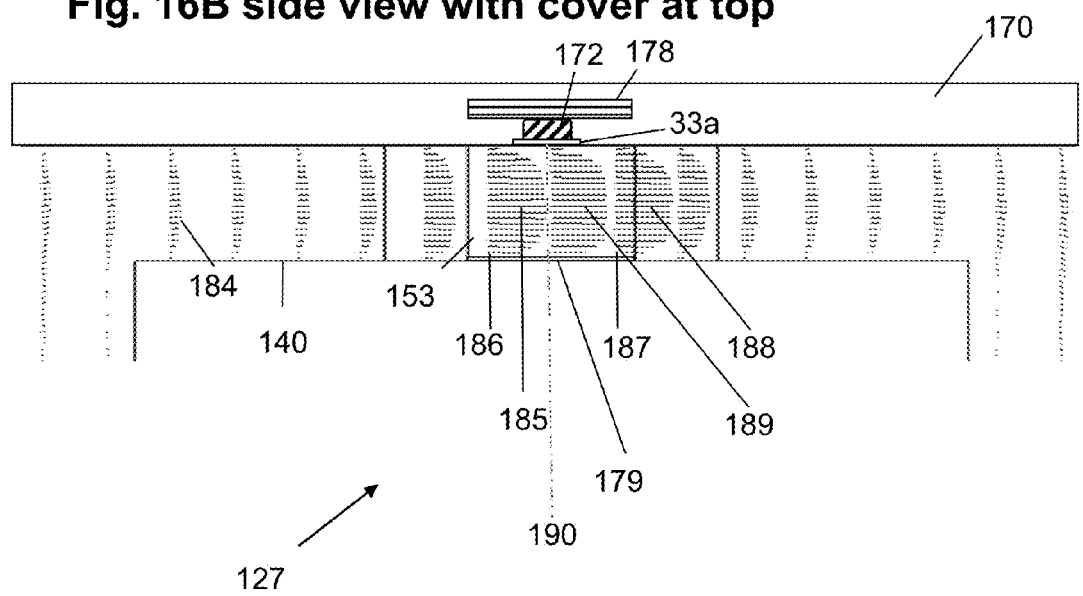

MICRO-OPTICAL CAVITY WITH FLUIDIC TRANSPORT CHIP FOR BIOPARTICLE ANALYSIS

CROSS REFERENCE TO RELATED APPLICATIONS

This application is a Continuation in Part application Ser. No. 12/034,640 filed on Feb. 21, 2008. This application claims priority benefit from U.S. Provisional Patent Application Ser. No. 60/902,685, filed on Feb. 21, 2007, which is incorporated herein by reference.

STATEMENT REGARDING FEDERALLY SPONSORED R&D

None.

BACKGROUND OF THE INVENTION

1. Field of the Invention

This invention relates to methods of analyzing biological specimens using biological micro-electromechanical systems (bioMEMs). The invention includes analysis methods and apparatus used as a microfluidic biosensor, optical resonator, and micro- and nanolaser device that measure optical properties of bioparticles including biological cells, organelles and molecules.

2. Description of the Prior Art

BioMEMs technologies derive from novel developments in materials and micro/nanofabrication methods. The prior art cited teach how to use these integrated technologies (e.g., microfluidics, electronics and photonics, and biocompatible surface chemistries) to create fluidic systems that are well suited to carry, manipulate, detect, analyze and process biological molecules, organelles, and whole cells. These systems also benefit from new light sources derived from semiconductors and solid state devices to enable efficient new tools for bioanalysis because they are small, easily integrated with microfluidics, and are well-adapted to microscopy and spectroscopy for imaging, flow spectrocytometry, and high speed analysis.

In prior art, U.S. Pat. No. 5,608,519 describes an apparatus and method for microscopic and spectroscopic analysis and processing of biological cells. The apparatus comprises a laser having an analysis region within the laser cavity for containing one or more biological cells to be analyzed. The presence of a cell within the analysis region in superposition with an activated portion of a gain medium of the laser acts to encode information about the cell upon the laser beam, the cell information being recoverable by an analysis means that preferably includes an array photodetector such as a CCD camera and a spectrometer. The apparatus and method may be used to analyze biomedical cells including blood cells and the like, and may include processing means for manipulating, sorting, or eradicating cells after analysis thereof.

The prior art describes a biocavity laser device developed for the analysis of whole cells in the geometrical optical regime $a \gg \lambda$ where the bioparticle radius $a$ is much larger than the wavelength $\lambda$ of the probe light wavelength. That prior art is limited in its scope since the preferred embodiment did not teach how to use optical cavities to analyze the full range of bioparticle sizes from the geometrical regime $a \gg \lambda$, to the intermediate Mie regime $a \approx \lambda$, to the Rayleigh limit $a \gg \lambda$. Cells are typically 10 microns or larger and exhibit multimode lasing properties. Micrometer- and nanometer-sized bioparticles in a cavity exhibit single mode lasing or no bioparticle-supported lasing at all, and are subject to different optical physics. Further, the prior art did not teach methods on how to relate the measured optical properties of small bioparticles to a biomolecular composition, nor did it teach how statistical distributions of these optical properties change from a normal to an abnormal or disease state. The prior art did not teach how to make fluid grates within a cavity to enable very high-speed parallel processing of small bioparticles. Nor did it teach how the microfluidic velocity distribution is related to the geometry and dimensions of fluidic structures within the cavity. Thus, there was no teaching on how to locate an analysis region in a cavity to optimize the fidelity, robustness, counting rates, and measurements of single bioparticles. Further, FIG. 4 of the prior art describes a preferred embodiment using micromachined channels in a silicon substrate with an attached gain region. This has the disadvantage for study of small bioparticles that side-scattered light in the channels is less accessible due to absorption.

SUMMARY OF THE INVENTION

This invention provides a method for rapidly distinguishing between diseased and normal cells using methods and apparatus amenable to a very wide range of bioparticle size. Moreover, this new technique has the potential of detecting disease at a very early stage using small bioparticles, a development that could change profoundly the way cancer is diagnosed and treated. To investigate tumors, pathologists currently rely on labor-intensive microscopic examination, using older cell-staining methods that can be time-consuming and may give false readings. The invention uses technology of BioMEMs, biosensors, microcavity optical resonators, and nanolaser devices to enable powerful new tools for the rapid, accurate analysis of optical properties of cells, organelles, and other bioparticles. The optical properties of bioparticles depend upon their geometry and biomolecular composition. The invention described here provides methods to relate measured optical properties to bioparticle size and refractive index. In turn, the invention shows how to relate the refractive index to the overall biomolecular composition. And, it shows how to quantify the way in which dominant and other biomolecules contribute to the refractive index. It reveals how the index changes with alterations in the distribution of biomolecules. The invention also provides methods for calibrating and maintaining the fidelity of measurements during operation of devices. It provides an apparatus for performing multiple optical measurements. The invention also provides an apparatus to flow, entrain, locate and analyze single particles one-by-one from a stream of particles in a fluidic optical cavity.

It is an object of this invention to provide an analysis method for resonant optical devices that relates the measured optical parameter to the biophysical properties of the bioparticles. These biophysical properties include the size, refractive index (or polarizability) and the biomolecular composition. It is surprising and advantageous that using this method to analyze a population distribution of a single optical property, such as the refractive index, can indicate the state of health or disease in whole cells and in isolated organelles.

It is also an object of this method to extract the refractive index distribution from the measured laser wavelength shift $\Delta\lambda$ distribution. It is also a surprising advantage that a bioparticle (as small as hundreds of nanometers in size) can be individually and rapidly (in microseconds) measured for its refractive index. It is also a surprising advantage that the optical properties can be directly related to the biomolecular composition of the particle, and that the distribution of the optical property among a population of like particles can be well-described by simple, analytic probability functions. When the biomolecular composition is altered as in a stressed or diseased cell, the optical properties and their distribution change in a manner that can be measured and analyzed with the statistical model.

It is also an object of this invention to make improvements to resonant cavity devices by incorporating methods for calibrating the measurements (providing a zero and scale factor) and for making corrections for any drift with time that may occur during the measurement procedure.

It is a further object of this invention to simplify the apparatus for measuring bioparticles by using a resonant optical cavity without a gain medium. This has the advantage of making the apparatus less costly to fabricate and facilitates both size and optical density measurement.

It is an object of this invention to provide the said analysis method to the improved apparatus and resonant optical device for the purpose of analyzing bioparticles.

It is also an object of this invention to provide a new method of operation of a micro/nano-cavity laser to analyze physical properties of very small bioparticles with size much less than the wavelength of light. The bioparticles can be isolated in solution or inside living cells.

It is an object of this invention to provide a new method for simultaneous detection, analysis, and manipulation of the bioparticles in a micro/nanocavity optical resonator.

It is an object of this invention to permit a fluid with a bioparticle (such as an inorganic material, biological entity like a cell, organelle, viron, or molecule) to flow through an optical cavity for particle analysis. The cavity comprises a fluid transport chip comprising a fluid grate with open channels between 2 reservoirs and interior reflective surfaces. Each channel has a cross-sectional area on the same order of magnitude as the cross-sectional area of the largest particle in the fluid, the volume of each reservoir being much greater than the volume of all channels. The optical cavity is completed with a cover for the channels having an inner surface in fluid tight contact with the first surface of the chip.

The invention presents new methods and apparatus that enable novel analyses of bioparticles and have wide ranging application for particle analysis, basic cell biology, cell culture, detection of disease, pathology, genetic engineering, environmental screening of toxins, pharmaceuticals, agricultural, and fermentation processes, biofuel production, and the like.

BRIEF DESCRIPTION OF THE DRAWINGS

The accompanying drawings and figures, which are incorporated in and form part of the specification, illustrate an embodiment of the present invention and together with the description, serve to explain the principles of the invention.

FIG. 13 shows a method for measuring properties of living cells.

FIG. 15a shows a top view of the fluid and particle flow in a microfluidic chip sealed with a reflecting cover structure to form an optical cavity. FIG. 15b shows a cross sectional view of the fluid and particle flow corresponding to FIG. 15a.

FIG. 16a shows a plan view of the completed cavity with fluid. FIG. 16b shows a cross sectional view of a preferred embodiment of this invention.

DETAILED DESCRIPTION OF THE INVENTION

Figure 1:
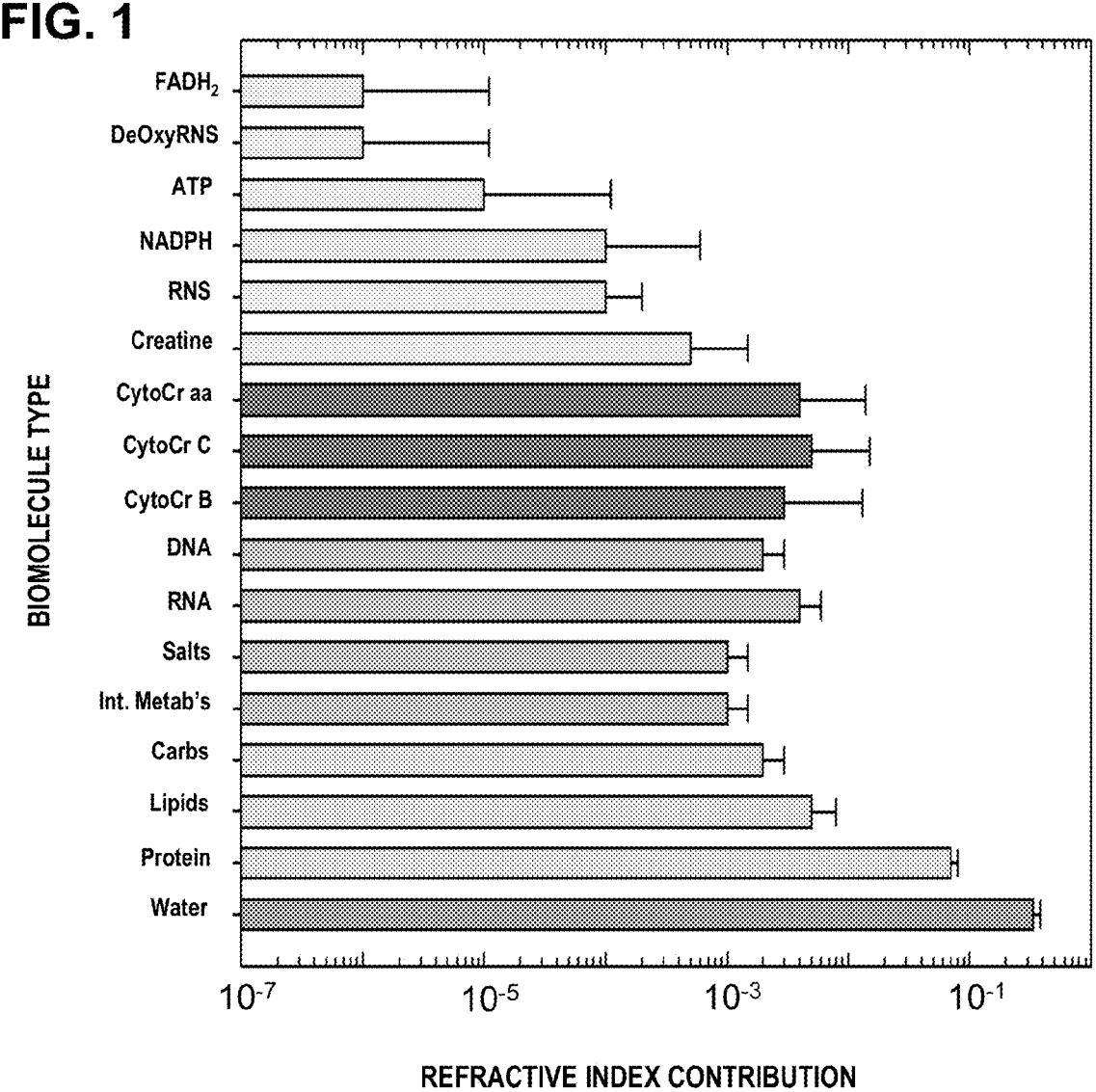
FIG. 1 shows the estimated contribution to the refractive index near 840 nm of representative biomolecules in a cell or organelle.

The invention also describes methods for analyzing bioparticles using resonant cavity devices to determining statistical properties of an optical parameter called $\Delta\lambda$ that is related to the biomolecular composition of the bioparticles. This enables a powerful analytical tool for studying disease in general in cells and organelles. Unlike any other single chemical or biophysical measurement, $\Delta\lambda$ is a measure of the overall biophysical state of the cell and organelles. The biophysical state of a cell is a reflection of its sum total of changes in biomolecular composition and organization. These properties can be used to differentiate normal and abnormal states of the particles by measuring distributions of optical properties among a population. It can also be used to identify healthy and diseased or stressed states of bioparticles derived from living cells or tissues.

The invention also provides a simple apparatus for multiple measurements, including size, morphology, and index, in a single device. And, the invention provides a new method for detecting and measuring physical properties of very small particles using light fluctuations arising from the interaction of bioparticles with resonant light waves within the cavity. The invention provides a new method for the simultaneous detection, analysis, and separation of small bioparticles using optical microcavities or nanolasers. Further, the invention provides means for isolating, locating, and analyzing bioparticles at high speed in a microfluidic optical cavity using the benefits of light interactions as high speed, non-contacting, and non-destructive.

By using these methods with such devices to detect and analyze intrinsic optical properties of biological specimens, considerable advantages are gained. One important advantage is that no fluorescent probes are needed so bioparticle populations can be analyzed in seconds to minutes with no special preparation for rapid front-end screening of specimen properties. The description of the analysis and apparatus here focuses on biomedical applications, but the present invention is not limited to biomedical and has application to other kinds of organic and inorganic particles as well.

This invention also relates to methods for analyzing data from resonant optical devices used to measure small particles like molecules, organelles, cells, virons and plastids or other small organic or inorganic particles (collectively called bioparticles here). Measurement of any optical property of bioparticles from any device benefits from this analysis. The method uses an optical property called $\Delta\lambda$ that represents the difference between a measured resonance wavelength of a bioparticle in a cavity and a reference wavelength. The discussion can be generalized to other optical measurements from a biosensor.

The invention includes laser analysis of small bioparticles (smaller than the wavelength of light) such as organelles using a phenomenon called "nano-squeezed light." The laser light is "nano-squeezed" through the organelle and a single lasing mode is supported. This squeezing effect results in a discrete band of laser light produced and a simpler spectrum to analyze compared to whole cells.

The invention uses optical cavities and optical resonators (the terms optical cavity and optical resonator are used interchangeably, herein) to measure biophysical properties of bioparticles. The optical cavity can take many different forms by using different materials, geometries, wavelength regions, surface treatments or means for coupling light into or out of the resonator. Generally, the cavity comprises highly reflective structures to confine light within a space. The space further includes space for fluidic specimens. The cavity has a means for coupling light into and out of the structure. The light may be generated internal or external to the cavity. The cavity allows the establishment of a resonance of light waves within the cavity and means to measure the resonance condition in the absence or presence of a specimen. The cavity may be constructed with materials such as dielectrics, metals, glasses, plastics, semiconductors, polymers or the like. The structure may take on different geometrical forms such as planar, box-like, rod, cylindrical, ring, spherical, or more complex shapes. It includes structures like waveguides, photonic lattices, periodic bandgap materials, or holey fibers. The geometry may include nanostructured components like quantum dots, arrays, wires, or layers. The inner surfaces of the cavity may further comprise surface treatments such as coatings, chemically functionalized surfaces, layers, processing, or thermal treatments to enhance the cavity optical performance or facilitate fluidic transport of specimens into and out of the cavity. In the discussion to follow, a planar mirror cavity forming a laser is used to illustrate the operation and method of analyzing bioparticles, and it is a preferred embodiment of the invention. However, the invention is not limited by this choice of geometry.

The laser works on the principle that the speed of light through a biological cell is slowed by the presence of biomolecules. By flowing a fluid, cells, or bioparticles through a semiconductor microcavity laser, these decreases in light speed can be registered as small wavelength red-shifts in the emitted laser output spectrum. The biocavity laser is used to measure this biophysical optic parameter $\Delta\lambda$, a laser wavelength shift relating to the optical density of cell or organelles that reflects its size and biomolecular composition. As such, $\Delta\lambda$ is a powerful parameter that rapidly interrogates the biomolecular state of single cells and organelles. The laser shift $\Delta\lambda$ can be viewed as a wavelength detuning (or alternately as a frequency detuning $\Delta\omega$) of the cavity resonance in dimensionless units as $\delta=\Delta\lambda/\lambda=\Delta\omega/\omega$ where $\lambda$ and $\omega$ are the fluid-filled cavity (without cell) resonance wavelength and frequency, respectively. Experimentally, $\Delta\lambda$ is measured in nanometers as the difference between a longitudinal laser mode of the fluid-filled cavity and the red-shifted laser wavelength produced by flowing cells or organelles (e.g. mitochondria) through the cavity.

Because of its importance, it is essential to properly interpret the measurement and make highly accurate measurements of $\Delta\lambda$. This invention improves upon the interpretation and accuracy of measuring $\Delta\lambda$ in the following ways:

1. It Provides a Means for Interpreting the Measurement.

The invention solves a technical difficulty in knowing exactly how the wavelength shift $\Delta\lambda$ relates to the biophysical properties (i.e. the diameter and refractive index) of the particle. Basically, the problem centers on determining the resonance frequencies of a particle in a planar active cavity with optical gain. The problem is not exactly solvable, but recent experiments on a variety of particles in various cavities have shown that a good approximation is given by a simple empirical relationship $$\Delta\lambda = kd\Delta n \tag{1}$$

where $\Delta n$ is the difference in refractive index between the particle and its surrounding fluid, d is the average particle diameter, and k is a constant relating to the geometry of the cavity. These results are an improvement over prior art that lead to inaccuracies in determining biophysical parameters.

2. It Provides a Means for Predicting the Distribution of $\Delta\lambda$ Among a Population.

Using the empirical relationship in Eq. 1, it is possible to develop statistical methods to predict how the probability distribution of $\Delta\lambda$ should depend on the biophysical quantities d and $\Delta n$. Experiments show that the probability distribution of diameters for a given type of bioparticle is very often approximated by a normal distribution function. This is not necessarily the case for the probability distribution of $\Delta n$.

3. It Provides a Means for Improving the Accuracy of the Measurement of $\Delta\lambda$.

The invention solves another technical difficulty relating to errors in the measurement of $\Delta\lambda$. $\Delta\lambda$ depends on the accurate measure of both the lasing mode wavelength the reference wavelength. Because of possible instrumental drift effects, the mode and/or reference wavelength may change with time and cause errors in the computation of $\Delta\lambda$. It is important to provide a means to correct for this drift to allow accurate computation of $\Delta\lambda$.

4. It Provides a Means for Absolute Calibration of the Measurement of $\Delta\lambda$.

The measurement of the $\Delta\lambda$ can sometimes be complicated by the calibration of the zero of measurement. Knowing the relationship between the measured property $\Delta\lambda$ and the biophysical properties can help determine the zero calibration of the measurement. This invention provides a method for calibrating the measurement of $\Delta\lambda$.

5. It Provides a New, Simpler Apparatus for Measuring Optical Properties of Bioparticles.

The invention provides an advantage over prior art to extract both size and refractive index properties of the bioparticle using multiple measurements in a single apparatus.

6. It Provides a New Method of Operation for Very Small Bioparticles of Size Less than the Wavelength of Light.

The invention provides a new means for measuring physical properties of very small particles using light fluctuations arising from the interaction of bioparticles with the resonant light waves within the cavity.

7. It Provides a New Method for Detecting, Manipulating and Separating Bioparticles.

The invention makes use of arrays of micro- or nanocavity resonators acting as lasers to probe living cells and bioparticles. The arrays can also act as optical traps to simultaneously trap and analyze bioparticles or separate them from other species.

8. It Provides an Apparatus to Flow, Entrain, Locate and Analyze Single Particles One-by-One in a Stream of Particles in a Microfluidic Optical Cavity.

It is an object of this invention to have an optical cavity which permits a fluid with a bioparticle (such as an inorganic material, biological entity like a cell, organelle, virion, or molecule) to flow through for particle analysis. The cavity comprises a fluid transport chip comprising a material substrate having a first surface fabricated with a pair of reservoirs extending deep into the substrate and separated by a barrier on the first surface fabricated with less deep channels interconnecting said reservoirs. Openings extend through a surface of the chip for transferring fluid between each reservoir and the exterior of the chip. Each channel has a cross-sectional area on the same order of magnitude as the cross-sectional area of the largest particle in the fluid, the volume of each reservoir being much greater than the volume of all channels. A first reflective surface layer is on the portion of the channels extending into the substrate furthest from the first surface. The chip substrate is formed of a material transparent to light emitted by the optical cavity. The optical cavity is completed with a cover for the channels having an inner surface in fluid tight contact with the first surface of the chip; and a second reflective surface, wherein the first and second reflective surfaces define the limits of an optical cavity including the channels.

Introduction

The optical properties of bioparticles depend upon their geometry and composition. Such bioparticles generally exhibit a variety of shapes and comprise a complex of biomolecules. Prior art U.S. Pat. No. 5,608,519 describes how the morphology (spheres, rods, disks, or more complicated shapes) can be determined by imaging microscopy and/or spectroscopic methods. The detailed internal distribution of molecules, like proteins, can be determined by separate, more costly, measurements such as 2-dimensional gel electrophoresis. However, these measurements provide only the distribution averaged over a very large number of bioparticles (~$10^9$) and cannot provide information about the variance from particle to particle in a population. This variance is critical for assessing the degree of normality or abnormality of the bioparticle. The invention described here shows how to determine the variance of biophysical properties in a population of bioparticles. It shows how to separate size and index contributions to an optical measurement. It also shows how the refractive index is related to the overall biomolecular composition. And, it shows how to quantify the way in which dominant and other molecules contribute to the refractive index. And, it shows how changes in the biomolecular composition will change the refractive index. The invention also allows means for calibrating and maintaining the fidelity of measurements during operation of devices.

Refractive Index of Biomolecular Solutions

In the present method the optical refractive index of a bioparticle is examined. The refractive index is directly related to other optical properties (dielectric constant, polarizability, susceptibility, birefringence, nonlinear optical parameters and the like) of the particle, and this discussion can also apply to these properties. The speed of light through a biofluid or biological cell is inversely related to its biomolecular concentration. In general, the refractive index n is related to the molecular absorption coefficient $\beta = \in M$, where $\in$ is the molecular extinction coefficient and M the molecular concentration, by the Kramers-Kronig relationship $$n(\varepsilon) - 1 = \frac{hc}{2\pi^2} P \int_0^\infty \frac{\beta(\varepsilon') d\varepsilon'}{\varepsilon'^2 - \varepsilon^2} \qquad (2)$$

where P is the principle value of the complex integral over photon energy $\in'$, h is Planck's constant and c is the speed of light.

The refractive properties of biomolecules originate in the electronic structure of their internal chemical bonds. Estimates of the refractive index contribution of biomolecules to the total refractive index of a bioparticle are shown in FIG. 1. The vertical axis (from bottom to top) shows decreasing prevalence of the molecule (water, protein, lipid, etc) in the cell. Most of the dry weight of a bioparticle is due to protein. Protein molecules possess covalent bonds that absorb strongly in the ultraviolet, but are mostly transparent in the visible and near infrared region where most semiconductors and solid state lasers emit. In general, the $\pi$-electron systems or proteins are the main origin of absorption in the 190-800 nm region. In small $\pi$-electron systems of proteins the absorption maximum occurs in the range 190-280 nm. The larger $\pi$-electron systems of the nucleic acid base units absorb near 260 nm and longer. Absorption beyond 400 nm occurs in the very large $\pi$-electron system of classes of chromophores and cytochromes that provide pigment to biomaterials. For example, many natural pigments arise from porphyrin and heterocyclic rings in chlorophyll, heme, and cytochrome oxidase found in mitochondria. The more extended larger $\pi$-electron systems of $\beta$-carotene absorbs between 400 and 500 nm. Previous experiments have shown that cytochrome complexes play an important role in the absorption spectra of cells and solubilized mitochondria in the visible and near infrared. These complexes comprise metal ions and large $\pi$ bonds that delocalize electrons, lowering optical transition energies into the visible range, between 500 to 700 nanometers.

Refractive Index of Bioparticles with Complex Composition

Whole cells or organelles comprise a complex milieu of thousands of molecule types, including those with heterocyclical molecular complexes and metal-containing porphyrin rings. The metal content of cells and mitochondria is found principally in the cytochrome proteins that are building blocks of complexes in the respiratory chain. The large $\pi$ systems of cytochromes play an important role in determining the refractive index in the visible and near infrared region of the spectrum where the cells are more transparent. And, each of the cytochrome molecules contributes to the refractive index at these wavelengths making it a sensitive measure of total cytochrome content. When certain genes are deleted or altered in cells or mitochondria, fundamental changes occur in cytochrome content and other pigmented molecules leading to changes in the refractive index that can be quantified by the optical properties.

Barer has shown a linear relationship between the refractive index and the biomolecular concentration as $n=n_0+\alpha C$ where $n_0$ is the index of the solvent, $\alpha$ the specific refractive increment of the molecule (specified by Eq. 2 or determined empirically), and C the concentration in grams per 100 ml. A change occurs in index $\Delta n = \alpha \Delta C$ arising from a change in concentration in a particular molecular species. More generally, the refractive index of a cell with many molecules of type i is given by the following equation, $$\Delta n_i = \sum_i \alpha_i C_i \qquad (3)$$

$$= \sum_{pigments} \alpha_{ci} C_{ci} + \sum_{proteins} \alpha_{pi} C_{pi} + \sum_{lipids} \alpha_{li} C_{li} + \ldots$$

where $\alpha_i$ is the specific refractive increment for biomolecule i (relative contributions vary as estimated in FIG. 1) and $C_i$ its concentration and the sum is over all biomolecules.

The refractive index contribution from a biomolecule increases as the product of the spectral weighting due to absorption in Eq. 2 and its concentration or biomolecular abundance in the bioparticle. Some structural biomolecules and osmolytes are tightly regulated by homeostasis, i.e. total water, protein, lipids, salt concentration and exhibit small uncertainty in abundance. These biomolecules form the basic cell structure and chemistry and require tight regulation to maintain cell viability. On the other hand, metabolic enzymes and metabolites exhibit a larger variation in abundance due to the existence of a wide dynamic range in respiratory states of cells or organelles like the mitochondrion. Some of these biomolecules vary several orders of magnitude in concentration without changing the basic structure or viability of the cell. These molecules typically occur in much lower abundance than the structural biomolecules.

Molecules with high spectral weight and abundance yield the highest optical density. Most of the functional structural molecules have high concentration but low spectral weight. On the other hand, respiratory enzymes containing pigmented biomolecules like cytochromes have high spectral weight but low abundance. Water is the primary contributor to the refractive index (accounting for 0.333), followed by structural proteins (about 0.06 to 0.08), cytochromes (about 0.007), and lipids (<0.005) and carbohydrates (<0.0002). These contributions to the index near 840 nm are summarized in FIG. 1. Chromophores and cytochromes stand out as unusual biomolecules because they are present in lower abundance but have the highest spectral weight for the refractive index in the visible and near infrared region of the spectrum.

Thermodynamics and Statistical Distributions of Molecules in Cells, Organelles, and Bioparticles A cell, organelle or bioparticle comprising a membrane bound solution of biomolecules has a refractive index that is higher than its surrounding fluid. This arises from a basic biological function of the cell membrane to selectively uptake of ions or molecules from the environment to concentrate them in the interior and assemble them into new biomolecules for increasing the cell functionality. A variety of passive and active mechanisms are used to establish these concentration differences, which in turn produce a differential pressure across the membrane. In thermodynamic terms, a function W can be defined that is the probability of finding a cell with a given biomolecular concentration C at a temperature T surrounded by a solution of concentration $C_0$. The theory of dilute solutions is used to illustrate this model. The osmotic pressure, here used loosely for any molecule enclosed by a semi-permeable boundary, is $P=(C-C_0)kT$ which is the well known van't Hoff relation. The net energy to raise the concentration from $C_0$ to C against the diffusive force is PV where V is the cell volume. If an ensemble of cells was treated in analogy to a population of particles in thermal equilibrium, the chemical potentials of the cytosols of each cell would be equal to the chemical potential of the exterior solution. In this case the differential probability of finding a cell with energy E is proportional to exp(-E/kT). The probability distribution would take the form $\Omega(\Delta C)\exp(-\Delta CV) \approx \Omega(N)\exp(-N)$ where N is the number of molecules. $\Omega$ is the number of accessible states, a rapidly increasing function of N conspiring with the exponential to produce a sharply peaked function in N. These arguments apply to precursor molecules and to biomolecules assembled from them.

Statistical physics can be used to describe this peaked function as the fluctuations in N, similar to fluctuations of particles in a gas or solutes in a dilute solution. The distribution in a fixed volume is $$W(N) = (1/\sqrt{2\pi})\exp(-(N-\overline{N})^2/2\overline{N}) \qquad (4)$$

where N is the total number of solute particles and $\underline{N}$ is the mean value of N. This distribution assumes that the volume of the cell is sufficiently large so that the deviation $N-\underline{N}$ is small compared with N. This is the case for large cells that contain the order of $\sim 10^{10}$ molecules like hemoglobin proteins in a red blood cell. There may be additional homeostatic regulatory mechanisms that place other restrictions on the deviations. On the other hand, there may be cells or organelles of much smaller volume such that the deviation is large compared to the mean. In this case, the distribution is given by Poisson's formula, $$W(N) = \overline{N}^N \exp(-\overline{N})/N! \qquad (5)$$

In this case, the distribution exhibits an asymmetric shape with a cutoff near low N and a long tail for high values of N. For example, mitochondria have volume $\sim 10^{-13}$ cm$^3$ with the number of biomolecules of a given prevalent type ranging from $10^2$ to $10^5$. Yeast cells have volume $\sim 10^{-10}$ cm$^3$ and biomolecules numbers some 3 orders of magnitude higher.

Statistical Distributions of Optical Properties of Bioparticles

The preceding discussion explains ideal distribution probabilities of molecules within cells. In biophysical experiments, the number of molecules may not be directly measured. Instead, an optical property (fluorescent intensity, optical density, phase contrast, spectral property or the like) may be more accessible. In this case, the probability distribution of the measured property has a more complicated dependence on geometry as well as biomolecular composition. A typical measured optical variable like a wavelength displacement or fringe shift or phase change or the like (collectively represented here by the variable $\Delta\lambda$) depends on the product of the particle diameter d and index difference $\Delta n$ as $\Delta\lambda = kd\Delta n$ where k is some factor specific to the particular optical variable being measured. Thus, $\Delta\lambda$ is expected to be the product of 2 or more independent and randomly distributed variables. In many cases d is a normally distributed variable.

If the $C_i$ in Eq. 3 are normally distributed variables (experimentally V is, and N from Eq. 2 is), then so is the probability distribution of $\Delta n$, with composite mean given by $\mu = \Sigma\mu_i$ and standard deviation given by $\sigma^2 = \Sigma\sigma_i^2$. The probability distribution for $\Delta\lambda$ then takes the form of a convolution integral of variables d (distributed with mean $\mu_d$ and deviation $\sigma_d$) and $\Delta n = \Delta\lambda/kd$ (distributed with mean $\mu_{\Delta n}$ and deviation $\sigma_{\Delta n}$), $$P_1(D) = Ae^{-(D-\mu_D)^2/2\sigma_D^2} \qquad (6)$$

$$P_2(\Delta n) = Be^{-(\Delta n - \mu_{\Delta n})^2/2\sigma_{\Delta n}^2} \qquad (7)$$

$$P_{12}(\Delta\lambda) = AB\int_{-\infty}^{\infty} P_1(D)P_2(\Delta\lambda/kD)dD \qquad (8)$$

This distribution function can be approximated through a transformation of $\Delta\lambda \to x = \exp(\Delta\lambda)$ that results in a log-normal distribution of the form $$P(x) = \frac{1}{x\sigma'\sqrt{2\pi}} e^{-(lnx-\mu')^2/2\sigma'^2} \qquad (9)$$

where x is the fitting variable, and $\mu'$ and $\sigma'$ are the log-normal fitting parameters. The Log-normal transformations $\mu = \exp(\mu' + \sigma'^2/2)$ and $\sigma^2 = (\exp\sigma'^2 - 1)\exp(2\mu' + \sigma'^2)$ are used to find the physical mean, standard deviation and variance of $\Delta\lambda$ of the distribution.

Figure 2A:
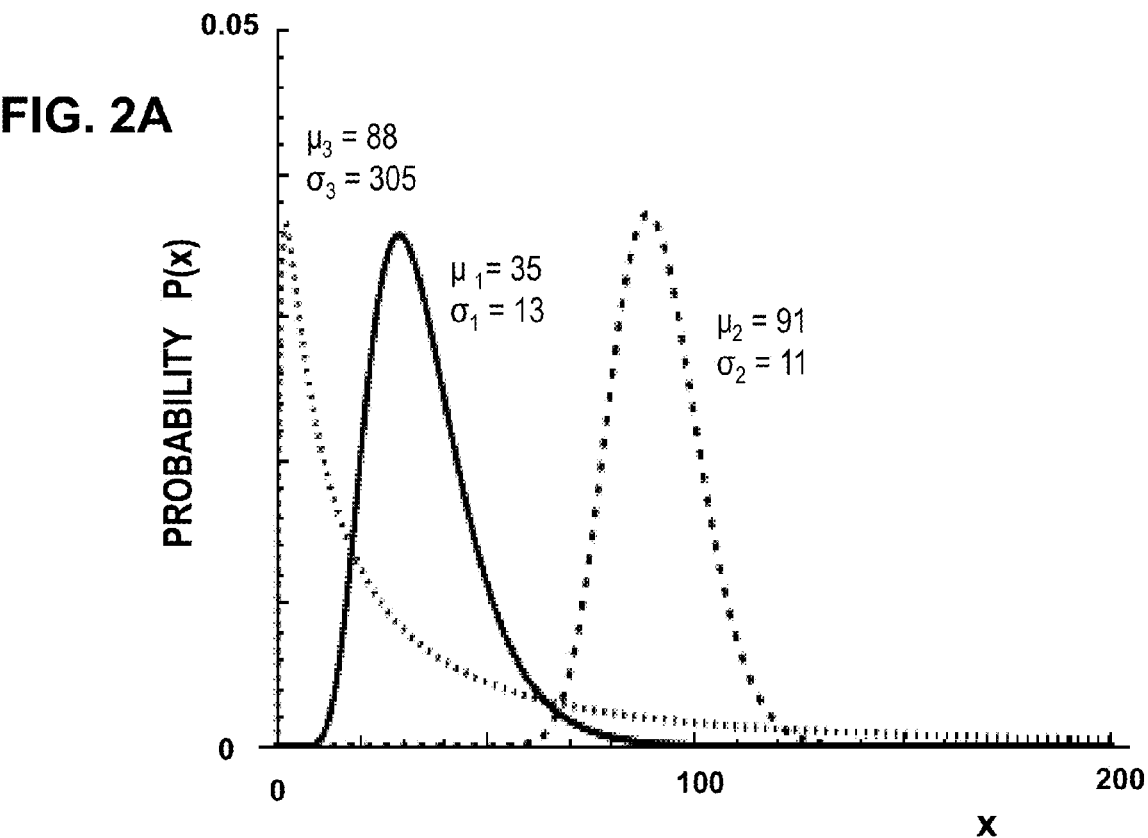
FIG. 2a shows the probability distribution functions for normal peaks and a highly divergent distribution.
Figure 2B:
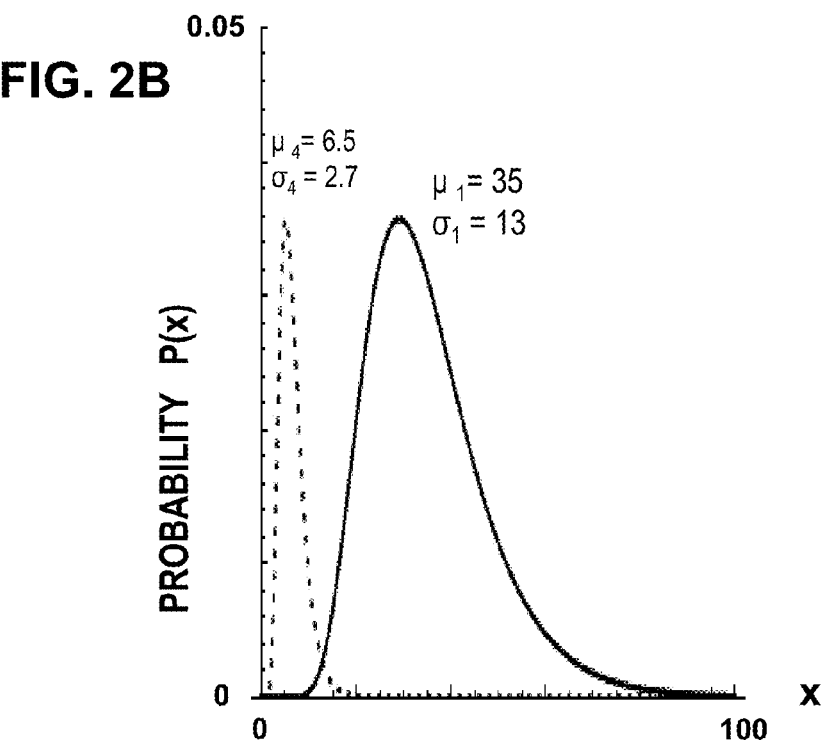
FIG. 2b Shows the probability distribution function representing for a normal peak and highly collapsed distribution.

FIGS. 2a and 2b illustrate two types of changes, divergence and collapse, that may occur as a result of biomolecular changes from a normal or regulated distribution. Other types of distributions are possible and might be described by other statistical functions beyond the log-normal distribution. The invention is not limited to log-normal distributions in the analysis.

The log-normal probability function P(x) is illustrated in FIG. 2a for three cases where the ratio $\mu/\sigma$ of the mean $\mu$ to the standard deviation a varies from a small to large value. For an intermediate value (solid curve with $\mu/\sigma = 2.7$) the distribution reveals a peak with long tail for large x. For larger ratios (large dashed curve on the right side with $\mu/\sigma = 8.3$) the distribution reveals a more symmetrical peak. Both of these distributions represent a normal or regulated distribution where the mean is larger than the standard deviation. For small ratios (small dashed curve on the left side $\mu/\sigma = 0.29$) the distribution exhibits a peak near the origin that is highly skewed to large x. This distribution applied to bioparticles is called a biomolecular divergence, for reasons explained hereafter.

FIG. 2b Shows the probability distribution function P(x) representing changes from normal, well-regulated biomolecular distribution among bioparticles (solid curve) to a highly collapsed distribution (dashed curve) characteristic of a second type of abnormal state (biomolecular collapse). These log-normal distributions show mean $\mu$ and standard deviation a parameters: (Right side) solid curve $\mu/\sigma = 35/13 = 2.7$ showing a peak with long tail for large x. (Left side) Dashed curve $\mu/\sigma = 6.5/2.7 = 2.41$ showing a peak collapsed to near the origin. The ratio $\mu/\sigma$ is the same for the 2 curves, the mean is 5× lower for the second curve.

Examples of Distributions Found in Practice

Figure 3:
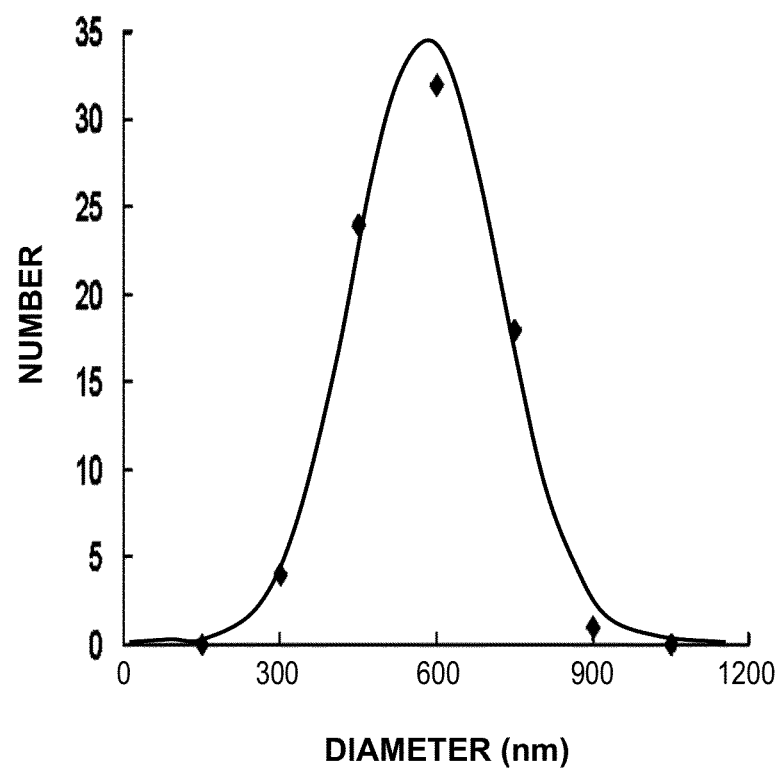
FIG. 3 shows a histogram of measured mitochondrial diameters.

Several classes of distributions for refractive bioparticles can be identified. A first class is a homogeneous (or intrinsic) distribution of bioparticles of similar type. These may be uniform in size (narrow size distribution) but less uniform in optical properties. This is a common case observed in experiments. For example, mitochondria fragment into nearly uniform-sized particles when the cells are stressed or when the mitochondria are extracted from the cells. Such a particle distribution is shown in FIG. 3.

Another example is the distribution of red blood cells that commonly occur with uniform size and biconcave geometries. Here the physical size is more tightly regulated than the biomolecular composition. The joint probability distribution (size and index) is reflective of the optical properties. On the other hand, the distribution may be uniform in optics (biomolecular composition) but comprise a broad distribution of sizes. In this case the joint distribution is more reflective of the size. This second case is less common. It is also possible to have both distributions exhibit a broad range. A second class of inhomogeneous (or extrinsic) distributions includes two or more dissimilar bioparticle types. In this case the distribution would be an additive superposition of multiple peaks representing each type. It would be possible to extract each component distribution by fitting the inhomogeneous distribution with a superposition of homogeneous distributions.

Another type of inhomogeneous distribution can occur within a homogeneous population when the individual bioparticles tend to aggregate or form clusters with two or more bioparticles. In this case the measured distribution is sensitive to the measurement technique. For example, high resolution imaging or nonlinear optical methods are still able to resolve individual bioparticles as they are sensitive to the bioparticle boundaries. Also the technique may sensitive to 2-dimensional or 3-dimensional effects and able to resolve the geometry of the cluster. On the other hand, some techniques (like total fluorescence intensity measurements) would only measure the total cluster volume and not measure individual bioparticle properties. However, it might still be possible to resolve discrete multiples of particles in the distribution of clusters.

The probability distribution for the particle size and/or the index difference may not be a normal distribution. In this case the analysis is more complicated, but the two distributions can still be approximately determined. The particle size distribution can be measured by some other technique like imaging microscopy (optical, confocal, near field optical, electron, atomic tunneling or force, or the like) or by flow cytometer or sizing methods or the like. Then, the measured distribution for the optical variable (fringe shift, wavelength shift, phase or contrast change, etc) can be deconvolved using the measured particle size distribution to render a probability distribution for the refractive index difference.

Spectroscopy Embodiment to Measure Optical Properties

Figure 4:
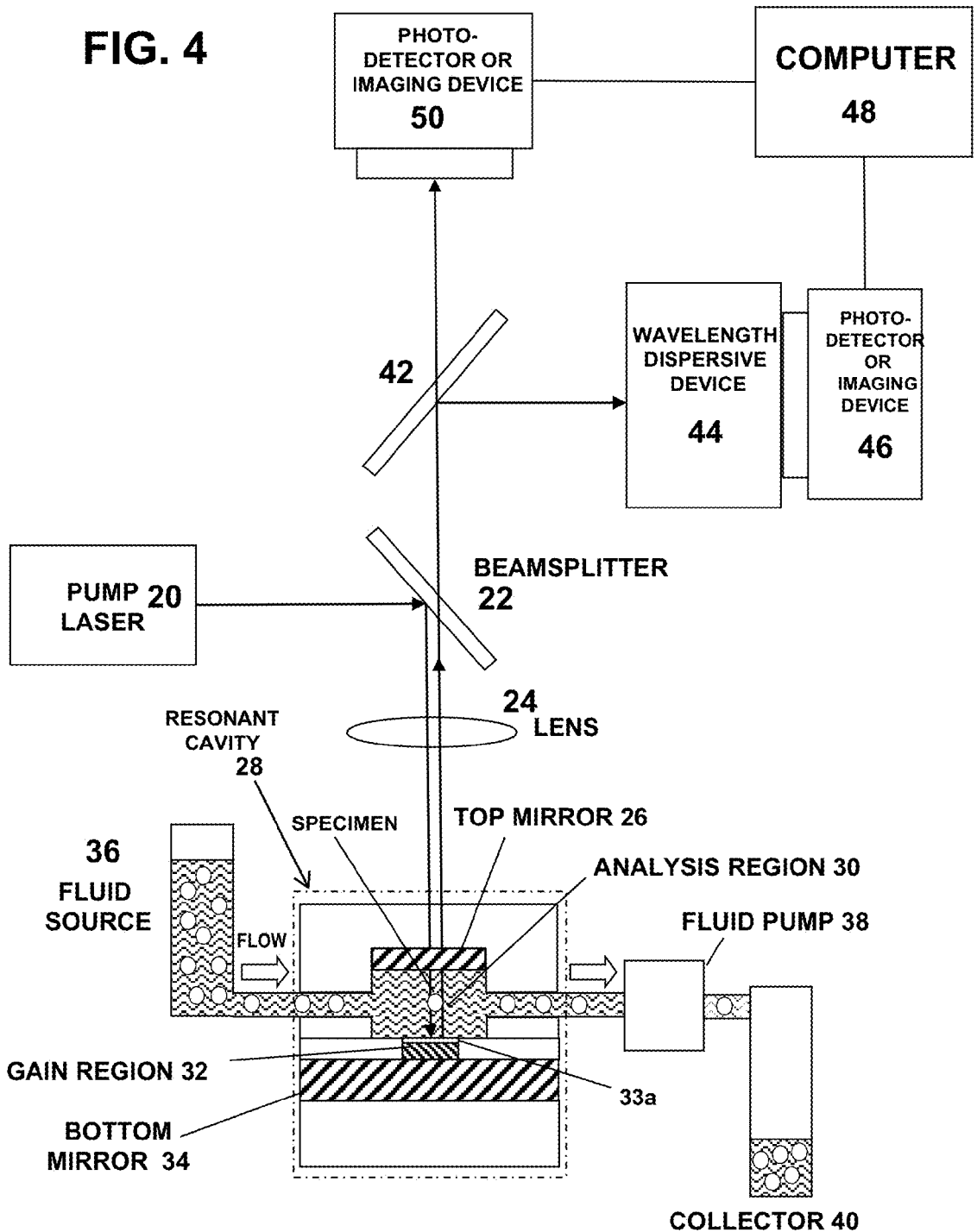
FIG. 4 shows a schematic of a biocavity laser apparatus.

An apparatus to measure optical properties of particles is shown in FIG. 4. It comprises a pump laser 20 emitting a beam that is directed by a beam splitter 22 through a lens 24 to a biocavity laser (resonant cavity 28) comprising a top mirror 26, a specimen in an specimen analysis region 30, a gain region 32 comprising a semiconductor and waterproof protective overlayer (not shown and can be an oxide, nitride, polymer, polyethylene glycol or polydimethylsilane, or organic compound), and a bottom mirror 34. Particles from a fluidic source container 36 flow through the analysis region with the help of a pump 38 to a collector 40. During transit, the particle passes through a gain region and triggers the biocavity laser to emit an intense beam that passes out of the cavity to a beamsplitter 42 where it is directed to an imaging device 50 and/or a wavelength dispersive photodetective device 44/46. Data from these devices are fed to a computer 48 for subsequent analysis. In the operation of the biocavity laser, the higher refractive index of a bioparticle (relative to the cavity with fluid only) triggers a lasing spectrum, and the spectrum is red-shifted relative to the cavity resonance without the bioparticle.

The laser technique has two important features. First, it is sensitive to small changes in bimolecular composition of cells. Tiny changes in laser wavelength can be detected since the laser linewidth is very narrow. So, the method is able to detect small biomolecular changes that occur with, stress, disease, or genetic manipulation. Second, the laser is sensitive to very small objects such as organelles like mitochondria and exploits a newly discovered nano-optical transduction method. Basically, this ultrasensitive detection of submicron particles uses "nano-squeezing" of light into photon modes imposed by ultra-small dimensions in a submicron laser cavity. The condition for nano-squeezing is that the organelle must be approximately smaller than the wavelength of light. This is a critical advantage of the biocavity laser. Because the mitochondria are so tiny (about 500 nm in diameter), it has been difficult to study them using standard light microscope or flow cytometry techniques. And, electron or atomic force microscopies may be limited to nonviable, fixed organelles so they cannot reproduce physiologic measurements. Thus the biocavity laser is an ideal tool for studying biomolecular changes in viable bioparticles.

The laser technique has a number of surprising features. The measurements can be self-triggering and self-calibrating and can be made in real time as particles flow in a microcavity. This is enabled by machine vision techniques whereby an algorithm can use binary image maps to located spectral position, peak width, and intensity and can be performed quickly. Further, the method is resistant to clustering of particles because of the nonlinear nature of the lasing process that requires a membrane-bounded bioparticle to operate.

Practical Results Obtained with Spectroscopic Embodiment

Experiments were performed to demonstrate the utility of biocavity laser spectroscopy to rapidly measure the effect of genetic disturbances in mitochondrial function. In one experiment a pair of mouse liver cell lines was used. One line was normal and the other line was transformed to cancer cells by carcinogens. The two cell lines were grown in separate, adherent tissue cultures. After growth to a large number of cells, the cells were removed from the tissue culture and suspended in solution. This removal has the effect of stressing the mitochondria which fragment into small particles of nearly the same size. That mitochondria fragment into nearly uniform-sized particles when cells are stressed is a surprising advantage that simplifies measure of optical properties. The mitochondria were removed from the cells for subsequent analysis by biocavity laser spectroscopy.

Micrographs of the isolated mitochondria were obtained by fluorescently labeling the mitochondria. FIG. 3 shows a histogram of the measured distribution of particle sizes, showing a mean diameter near 600 nm and a standard deviation of about 100 nm. The histograms is well-described by a normal Gaussian distribution (solid line). The mitochondria were suspended in phosphate buffered saline (PBS) without calcium or magnesium and flowed through the biocavity laser. Spectra were collected and the resulting laser peak shifts $\Delta\lambda$ (relative to fluid-only) were analyzed. Delta $\lambda$ is measured in nanometers as the difference between the reference wavelength of the biocavity laser, and the wavelength of red-shifted laser light that cells or mitochondria emit as they flow through the biocavity laser. It is a function of the refractive index difference between the cells or mitochondria, and the surrounding aqueous medium (PBS) and particle size. Since refractive index is a function of biomolecular composition and concentration, mitochondria that contain more chromophores and cytochromes will show greater peak shifts.

Figure 5A:
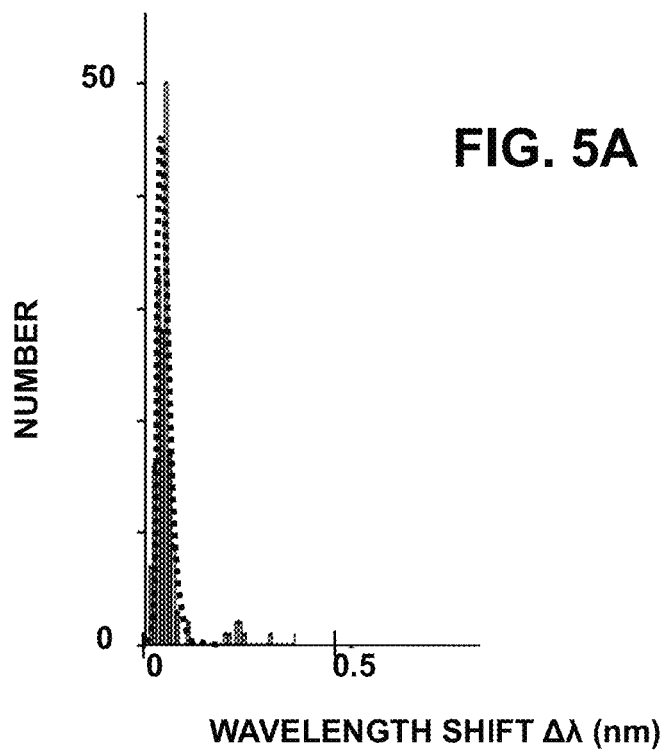
FIG. 5 shows histograms of laser wavelength shifts for isolated mitochondria from cancer (FIG. 5a) and normal (FIG. 5b) mouse liver cells.
Figure 5B:
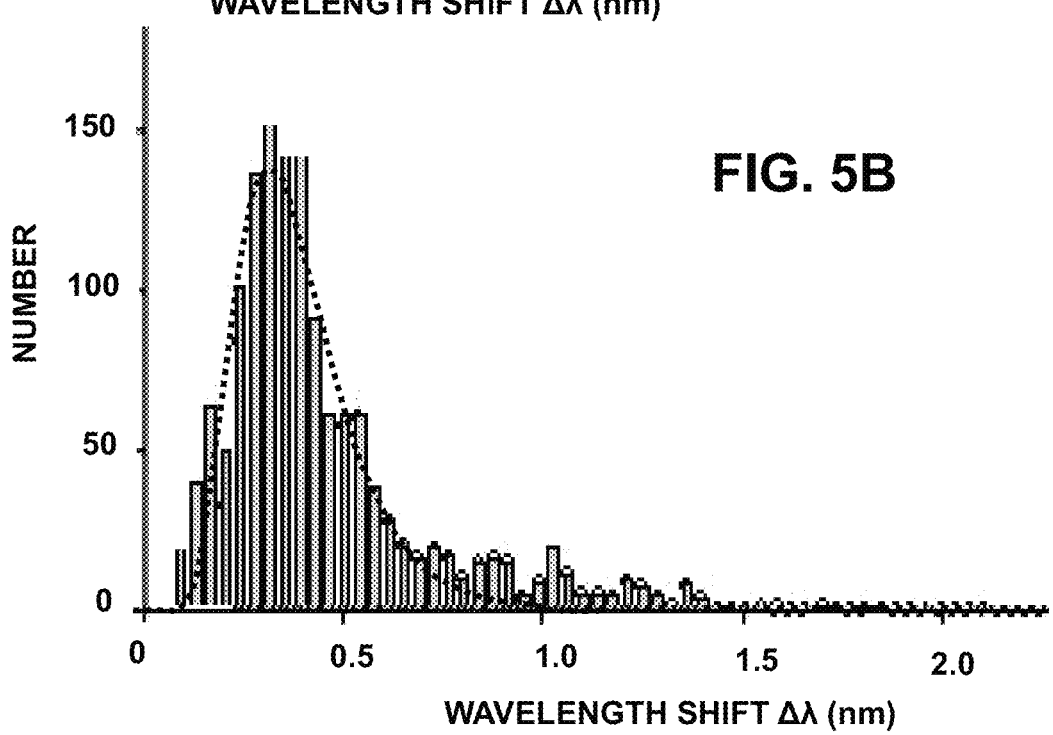

The statistical variation of $\Delta\lambda$ within each population was studied and modeled. The population distributions of $\Delta\lambda$ obtained with mitochondria from normal cells (FIG. 5b) and cancer cells (FIG. 5a) reveal striking differences in mean and standard deviation. Normal mitochondria produced a distribution with a single peak with mean near 0.4 nm and tail to longer wavelength. The shape of this distribution can be fit with a log-normal distribution. In contrast, abnormal mitochondria produce a peaked distribution with an approximately 10 times lower mean value and standard deviation. These features reflect a collapsed state of stressed or diseased cells that have a greatly changed composition of biomolecules in the mitochondria. This altered composition reflects a large decrease in biomolecules like chromophores and cytochromes that contribute to the refractive index. The loss of these molecules in the mitochondria represent a greatly lowered biochemical reducing ability of the electron transport chain. This represents a decreased metabolic activity. These observed changes observed in the spectra of normal healthy mitochondria to those of mitochondria in the cancer state indicate that the technique has the ability to rapidly diagnosis healthy and disease states.

The log-normal distribution provides the best, self-consistent fitting function to these data. The fitting function (dotted lines) shown in FIGS. 5a and 5b accurately describe the shapes of the measured distribution functions. The single fitting function Eq. 9 with only 2 adjustable shape parameters describe the date much better than Gaussian or Poisson functions discussed earlier.

Another experiment was carried out to simulate the effect of neurological diseases effects like Alzheimer's disease on mitochondria. In the electron transport chain of the mitochondria, a potential is established by internal membrane pumps that transport protons across the inner membrane. Exposing mitochondria to high $Ca^{++}$ gradients causes breakdown of an inner mitochondrial membrane potential, with attendant creation of megapores, organelle swelling, and release of toxic cytochrome c into the cytoplasm. In an experiment, mitochondrial isolated from a separate line of mouse liver cells were suspended in a buffer solution for flow experiments. One suspension was used as the control. And a separate solution of CaCl ranging from 10 to 1000 µM was added to produce an insult to the organelle and induce formation of a megapore and swelling. The organelles were flowed for a few minutes and the emitted spectra were recorded and analyzed to extract spectral parameters such as spectral wavelength, linewidth, intensity and others. These parameters were summarized in histograms shown in FIGS. 6b (normal) and 6a ($Ca^{++}$ insulted) to show the parameter mean values and their statistical variation among the cell suspension.

Figure 6A:
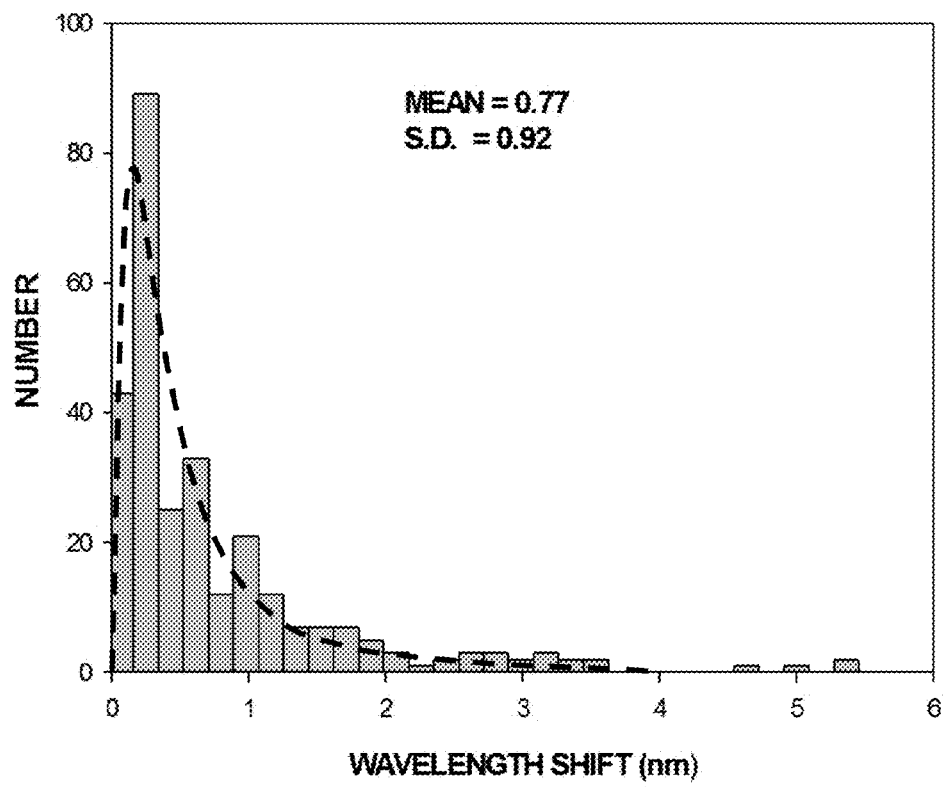
FIG. 6 shows histograms of laser wavelength shifts for mitochondria isolated from normal mouse liver cells (FIG. 6b) and then subjected to Ca++ concentrations to simulate a disease state (FIG. 6a).
Figure 6B:
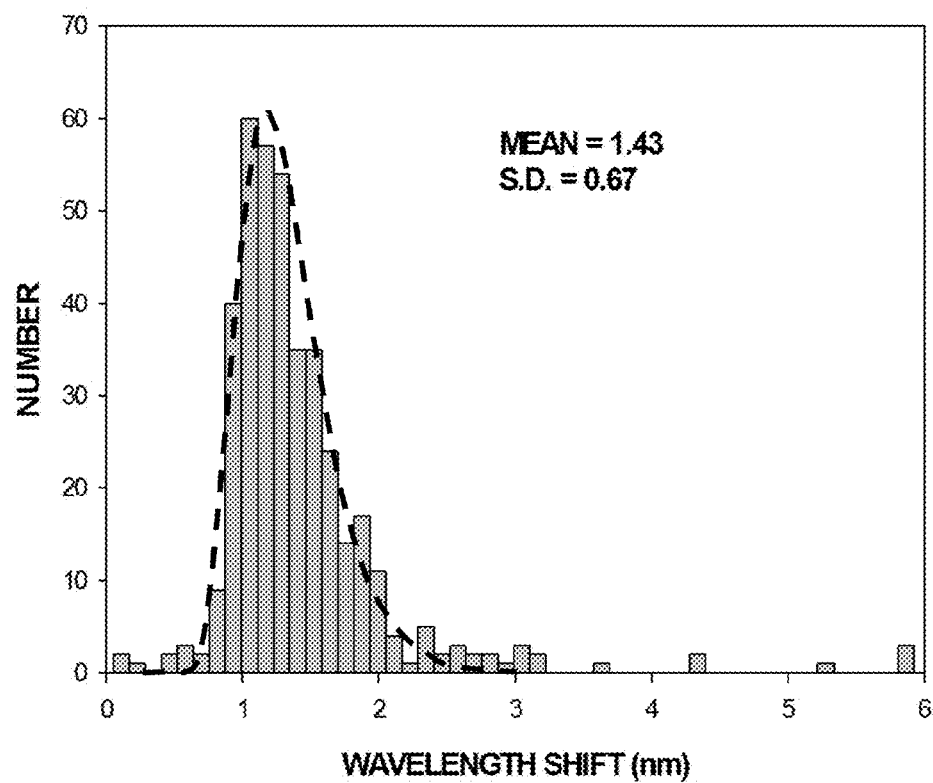

These data of FIG. 6b show that the control suspension without $Ca^{++}$ reveal a singe $\Delta\lambda$ peak near 1.4 nm wavelength shift with standard deviation of about 0.67 nm. The histogram is well described by a log-normal distribution (dashed line). The histogram for the control mitochondria suspension with the addition of a 1000 µM $Ca^{++}$ solution is shown in FIG. 6a. These data are significantly changed from the control sample and exhibit a lower mean and much larger variance. These insulted mitochondria exhibit a biomolecular divergence whereby $\Delta\lambda$ is peaked near 0 but is spread to much larger values as well. This distribution is also well described by a log-normal distribution (dashed line) with lower mean and larger standard deviation. Using the log-normal analysis of these data clearly shows that the optical density in the mitochondria has changed due to decreases in their refractive index and biomolecular composition. The biomolecular composition changes because the organelles swell and lose cytochrome content. The statistical analysis provides guidance in calibrating the spectra as well as the determining the shape of the distribution.

Calibration of the Measurements

Once the distribution of $\Delta\lambda$ is measured, it is important to calibrate the spectral distribution. The calibration scale comprises a zero and a scale factor. The scale factor can be set by using a calibrated spectrometer or the like or measuring system response for two or more sources with known wavelengths. Determining the zero is more difficult. Prior art used a spontaneous emission wavelength set by a longitudinal mode of the resonant cavity without a bioparticle. Alternately, prior art U.S. Pat. No. 5,608,519 used stimulated emission near a longitudinal mode. These reference wavelengths are helpful, but do not necessarily determine the zero wavelength with high precision.

With regard to calibrating the zero position, it is important to measure and correct for any drift with time that may occur during the measurement. One method to determine the zero is to measure a pre-existing cavity mode that is independent of the bioparticle. By tracking such a mode as a function of time during the measurement, it is possible account for any drift or sudden perturbation of the cavity. In this case, either a spontaneous or stimulated emission wavelength established by the resonant cavity independent of the particle being measure is recorded as a function of time. This measurement can be recorded simultaneously or periodically with the measurement of $\Delta\lambda$ for the particle or measured periodically and then interpolated for an arbitrary time. Thus a reference wavelength is available for every measured shift arising from a bioparticle. This enables the system drift with time to be can be determined. Then, the measured spectra can be corrected for any effects of drift.

In the absence of a reference mode, a method for calibrating the zero is to use a homogenous fluidic specimen. In this case, each small volume of the fluid containing many bioparticles (the order of hundreds) is representative of the properties of the whole sample volume. Each small volume sample has the same average properties. The moving average of each small volume can then be used to correct for drift of the zero calibration. Another method of calibrating the zero is to fit the moving distribution of several volumes with the probability function using zero as an adjustable parameter. Knowing the form of the distribution function enables the zero to be determined with higher precision. Using these method, it is possible to accurately record the experimental distribution of measured values of wavelength shift without measuring any reference wavelength.

Microscopy Embodiment

Figure 7:
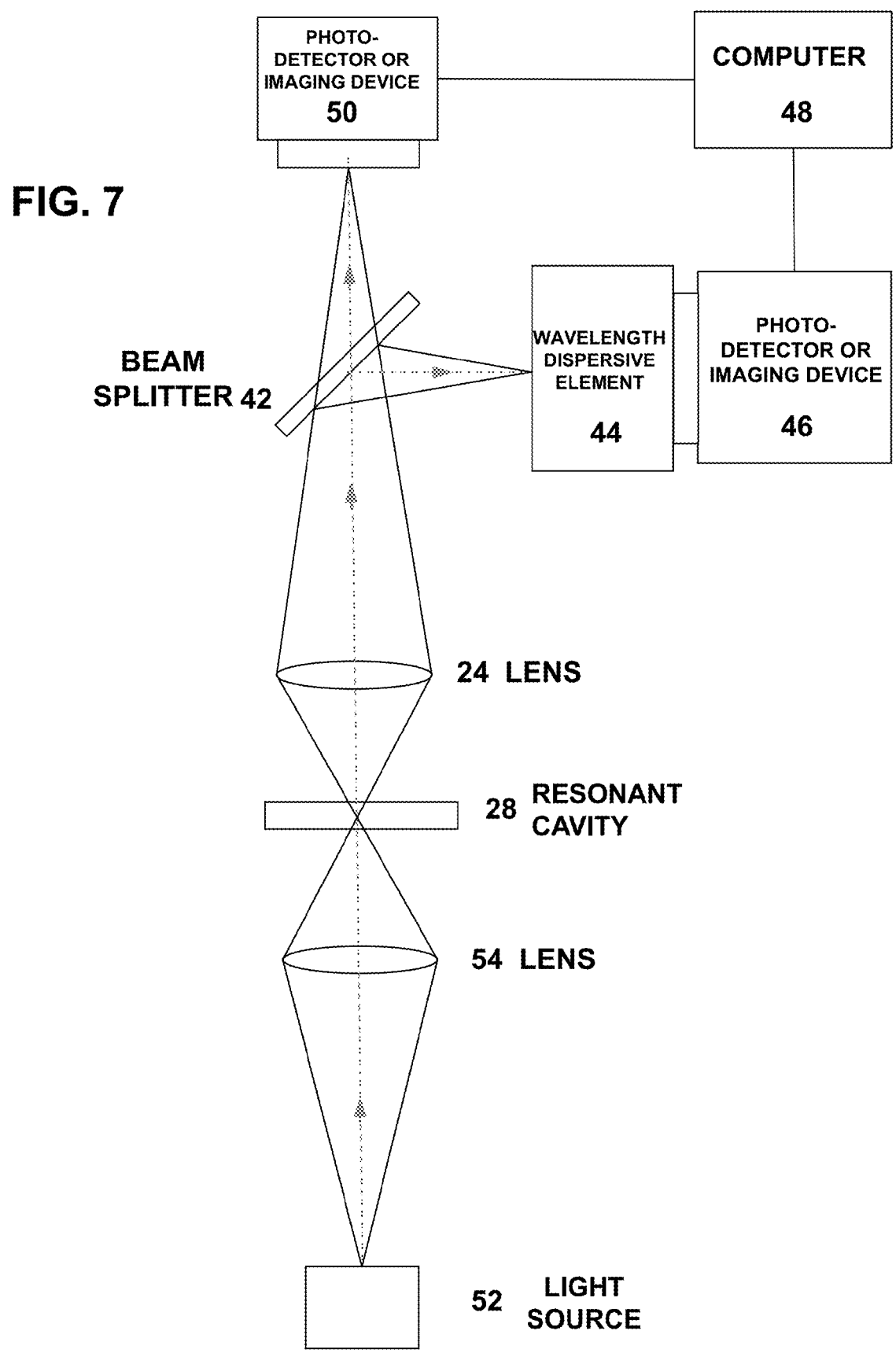
FIG. 7 shows an Apparatus for measuring optical properties of bioparticles in a resonant optical cavity.
Figure 8A:
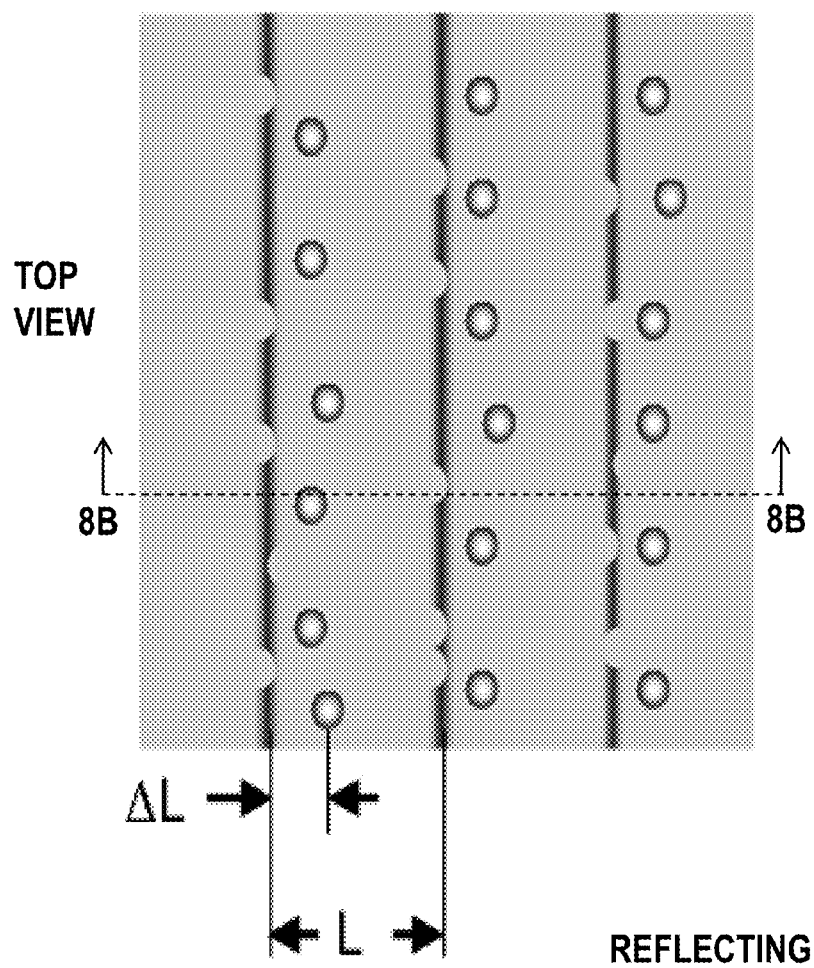
FIG. 8 shows a schematic of a graded, resonant optical cavity for measuring optical properties of bioparticles, (top view FIG. 8a and side view in FIG. 8b) and binary image from an experimental cavity (FIG. 8c).
Figure 8C:
Figure 8B:
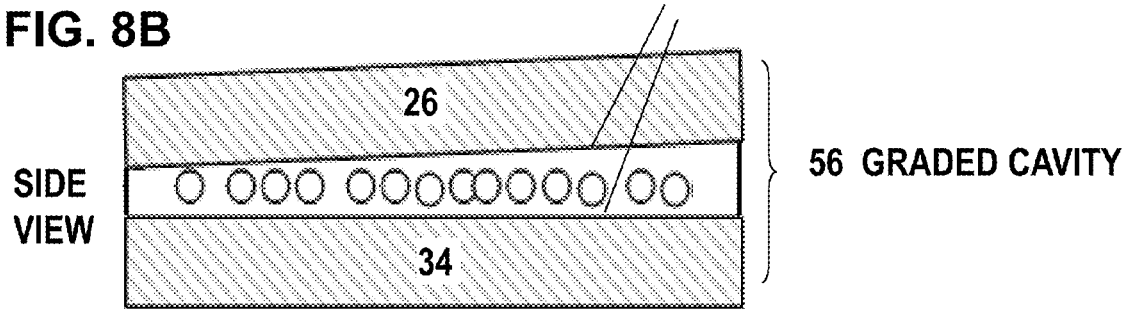
Figure 9:
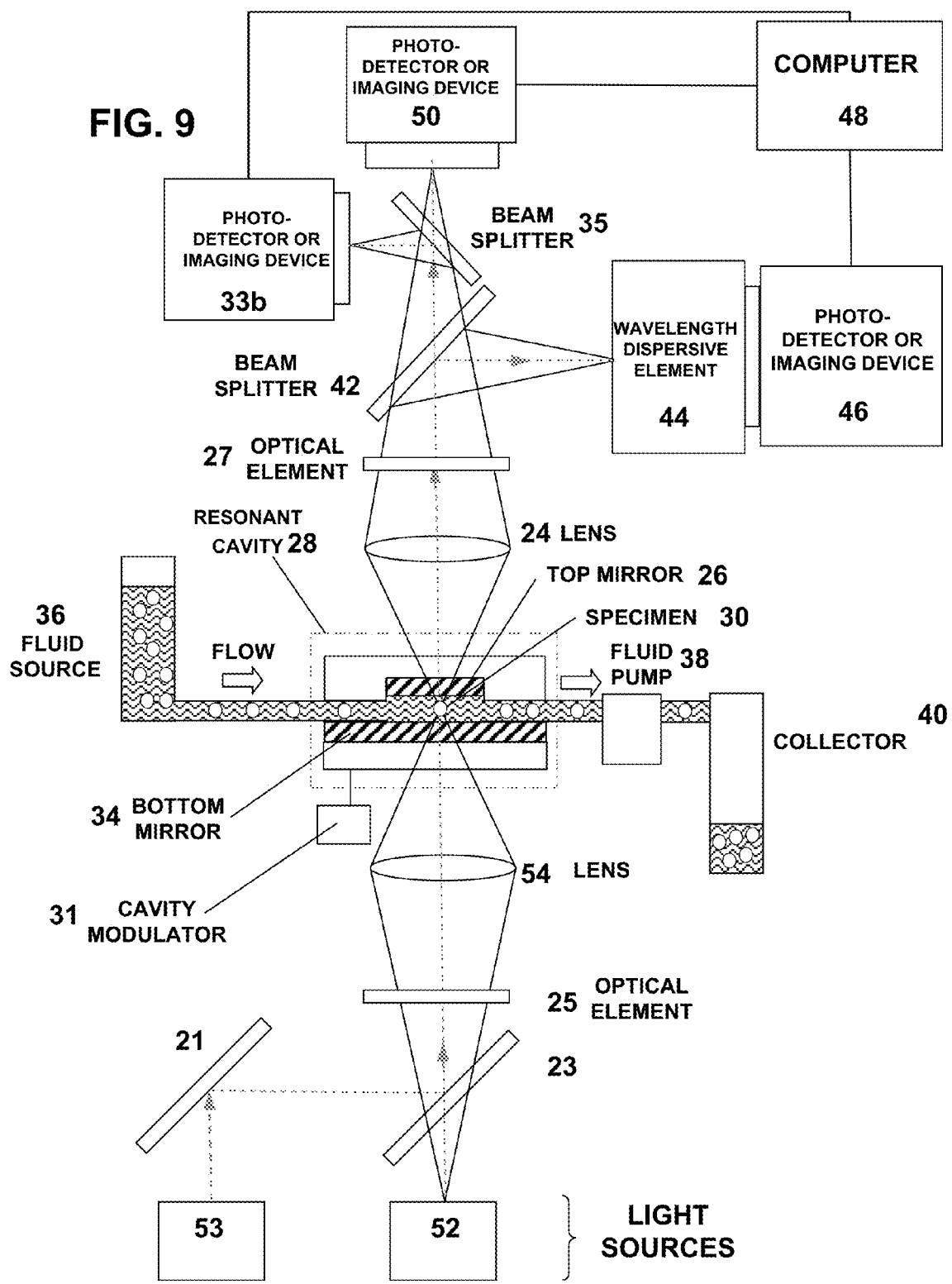
FIG. 9 shows an enhanced apparatus for measuring optical properties of bioparticles.

Another embodiment of the measurement and analysis method is to use multiple beam interference microscopy with an apparatus shown in FIG. 7 through 9. In FIG. 7 light from source 52 is directed toward a resonant cavity (with or without gain) 28 with lens 54 and then the image of the cavity is relayed with lens 24 to a imaging device 50 and/or to a spectroscopy/detector device 44/46. The output of these devices is linked to a computer 48 for analysis. The light source could be a laser, LED, lamp, fiber optic source or the like. Alternately the light source could be contained in the cavity (semiconductor, fluorescent material, or the like). The light interacts with the cavity to establish optical resonances that can be observed by a detector. These conditions can be detected by the imaging device or spectral device. When bioparticles are inserted into the cavity, the light interacts with the particle/cavity and produces a light signal (transmitted, reflected, scattered, fluorescence or the like) that is modified by the bioparticle and can be analyzed by spectrometer or microscope equipped with a photosensitive detector (PMT, PD, video camera, CCD, or the like) to record images. FIG. 7 shows a transmittance apparatus as a preferred embodiment, but the invention is not limited to this arrangement and could also take the form of a reflectance, scattering, or fluorescence arrangement or combination thereof.

In one embodiment, the resonator is preassembled and the specimen is brought into and out of the resonator, usually in a fluid by force of injection, flow, pump, vacuum, gravity, electrokinetic, or the like. In another embodiment, the resonator is not preassembled but comprises components. The specimen is applied to the components, for example, by application of a fluid onto a surface using a drop, smear, brush appliqué, paint-on, spray, or the like. The specimen may remain wet or be allowed to dry, and the resonator is assembled to contain the specimen for further analysis.

In a preferred embodiment, the cavity is graded in space as in FIG. 8 and the resonance conditions are mapped across a 2-dimensional space for a planar cavity. The resonance conditions render images with a variety of intensity variations. The locus of intensity maxima occur as contours where the cavity is in resonance. There is a dark background where the cavity is out of resonance. With bioparticles present, the contours are locally altered. Some particles shift the cavity out of resonance while others shift it into resonance. This is illustrated in FIG. 8 for a simple graded planar cavity where the resonance conditions are rendered as spaced interference fringe images. The resonance conditions in a medium of refractive index $n_1$ for neighboring fringes in the cavity with spacings $d_1$ and $d_2$, respectively are $$n_1 d_1 = m\lambda/2 \qquad (10)$$

$$n_1 d_2 = (m+1)\lambda/2 \qquad (11)$$

where m is the order of the fringe and $\lambda$ is the wavelength of light. The spacing L of the fringes is given by $$d_2 - d_1 = L \sin\theta \qquad (12)$$

where $\theta$ is the wedge angle of the cavity. When an object of height h and index $n_2$ is placed into the cavity, the fringes will be locally displaced at the object. If the optical thickness $h\Delta n$ where $\Delta n = n_2 - n_1$ is small compared to the optical thickness of the cavity $n_1 d$ then the observed fringe displacement $\Delta L$ will be less than L and determined by the relationship $$h\Delta n = \Delta L/L\lambda/2 \qquad (13)$$

Thus, the optical thickness of the object is the relative fringe displacement $\Delta L/L$ times a half wavelength. If the particle height is known, the index can be determined from the fringe displacement. For a group of said objects (cells, organelles, bioparticle or the like) the statistical distribution of the refractive index can be determined from the distribution of fringe shifts as described in the previous section.

In FIG. 8c the bright line to the left side of the image is the undisplaced cavity fringe (the next order fringe is not shown). The fringe line is disrupted by dark areas corresponding to bioparticles out of resonance. On the right side of the image, other bioparticles in resonance appear as bright spots. The displacement of the bright spot from the fringe line is a measure of the bioparticle optical density $h\Delta n$. These bioparticles are also directly imaged and their diameters and morphology can be determined. The measured diameter closely approximates h and $\Delta n$ can be determined with Eq. 13.

Another embodiment of the apparatus is shown in FIG. 9. FIG. 9 also includes multiple light sources 52 and 53 and multiple detectors 50, 33, 44/46 and multiple beamsplitters 42 and 35 for recording combinations of light wavelengths for imaging/spectral measurements of transmittance, reflectance, scatter, phase, absorption, fluorescence or the like. When used in combination with the resonance measurements, these additional measurements provide advantages in identifying bioparticles and measuring additional optical properties FIG. 9 also includes means for flow of bioparticles using elements 36, 38, and 40 to allow bioparticles to be injected or flowed through the cavity. FIG. 9 includes imaging (elements 33 and 50) and spectral means (elements 44 and 46) for detecting resonance conditions. It also includes a computer 48 for analysis including machine vision methods.

FIG. 9 also includes a means (element 31) to modulate the cavity spacing, geometry, phase, reflectivity, Q or the like to enhance measurements of large numbers of particles. For example, the resonance conditions can be modulated across the field of view by scanning the cavity spacing d by mechanical, acoustic, electrical, magnetic, piezoelectric, optical, or other means. This has the effect of moving the fringes across the field of view such that more particles can be analyzed. In this case the local fringe displacement by a particle is recorded in successive images of moving fringes. It is also possible to scan the cavity in space, scan the light source in space or in wavelength to expedite the analysis.

FIG. 9 also includes means (element 25) for modulating, steering, scanning, pulsing or holographic control of the input light. It also includes a means (element 27) for lenslet array or holographic or phase contrast methods including an intensity variation due to the phase of the particle. A spatial profile of the intensity I(x) may be measured as $$I(x)=1\pm 2\phi(x) \tag{14}$$

where $\Phi(x)$ is the phase of the particle approximated as $$\varphi = \frac{2\pi}{\lambda}\Delta n d \tag{15}$$

In this method the intensities of the particles are recorded and a distribution of optical densities is obtained.

It is also possible to calibrate the cavity by using standard particles of know size, refractive index, and fluorescence properties. And, it is possible to use cavities with fixed, multiple steps in spacing to aid in calibration. This apparatus has the advantage that it can use a single image to simultaneously obtain a measurement of a reference feature, specimen optical density, and specimen size. The technique can also use machine vision and algorithms to create binary image maps to located spectral position, peak width, and intensity and can be performed quickly. The method is amenable to measuring bioparticle clustering because the clusters can be directly imaged and can be differentiated from single particles.

An advantage of this embodiment is that multiple light sources using similar or different wavelengths and detectors at similar or different wavelengths can be employed to obtain simultaneous information on the optical properties in the image, including fringe displacement, phase, fluorescence, brightfield, darkfield, scatter, reflectance, transmittance, and the like. A further advantage is that there is no drift in the measurement as the zero correction is automatically included in image. Also the procedure can be done wet (flow or static fluid) or dry (higher contrast but in a dry state).

New Mode of Laser Operation for Small Bioparticles Using Light Fluctuation Measurements There are three regimes of operation of the optical resonators as a laser, according to bioparticle size. In the geometrical limit where the particle radius a is much larger than the wavelength $\lambda$ of light, $a \gg \lambda$ the laser is called a biocavity laser that exhibits multimode spectra that are useful for studying particle morphology, shape, and composition. In the intermediate Mie regime, where $a \approx \lambda$, the laser is called a nanolaser and exhibits a phenomenon of nano-squeezed light with single mode (both single longitudinal and single transverse mode) operation. In this mode, the spectra are simpler and useful for studying particle size and composition. In the Rayleigh limit where $a \gg \lambda$ the bioparticles scatter light isotropically and do not support intracavity modes. Instead, the laser is used in a new way to measure laser cavity mode fluctuations arising from scattering from nanoparticles. These fluctuations can be used to study nanoparticle mass, shape, motion, and interactions with other particles and materials.

Particles larger than the wavelength of light produce the scattered field that peaks in the forward and near backward directions in contrast to smaller particles, which scatter light more uniformly. The angular width θ of the forward peak, is proportional to the ratio of the wavelength $\lambda$ to the particle's size a as θ≈λ/a. As the particle size decreases to the Mie regime, the scattering angle increases but is predominantly in the forward direction. As the particle size decreases further into the Rayleigh limit, the scattering angle becomes very large. Finite difference time domain calculations predict that the transition from Raleigh to Mie scattering occurs near bioparticle diameters near 200-300 nm.

In the geometrical and Mie lasing regimes, light cycles through the particle, cavity, and semiconductor gain region till a stable mode pattern is formed. Light scattered at small angles is reflected multiple times in the cavity and builds up stable lasing modes in the lasing process. In this manner, bioparticles inside the laser cavity serve as optical waveguides to confine light generated in the resonator by the semiconductor. The waveguiding effect is due to slight differences in the dielectric constants between various cell components and the surrounding fluids. The laser operates at resonant frequencies established by the dielectric properties of the cells. By using a high resolution spectrometer or interferometer, these lasing frequencies can be resolved into narrow spectral peaks. In the Raleigh limit, the particle behaves as a dipole and radiates in all directions. The large angle scatter light is lost sideways from the longitudinal cavity. The Rayleigh mechanism tends to scatter light at large angles relative to the incident beam. Thus, these tend to be loss mechanisms for operation of the laser which operates principally with light in the forward and backward directions.

Operation in the Mie Regime

Bioparticles with size near the wavelength of light fall into the Mie regime where nano-squeezed light (light squeezed in space) is present in the laser. The approximate condition for nano-squeezing at 850 nm for 100 nm spectral gain bandwidth gives a 500 nm. Thus, the condition for nano-squeezing is that the bioparticle must be approximately smaller than the wavelength of light. Operation of the laser in the Mie regime is useful for quantifying changes in biomolecular composition that contribute to the intrinsic refractive index.

Using nano-squeezed light conditions, the laser has recently been used to study biophotonic properties of genetically modified mitochondria of several hundred nm in size isolated from animal and yeast cells. Because the mitochondria are so tiny, it has been difficult to study them using standard light microscope or flow cytometry techniques. And, electron or atomic force microscopies are mostly limited to nonviable organelles so they cannot reproduce physiologic measurements. The nanolaser is an ultrasensitive method of detection for submicron particles that uses nano-squeezing of light into photon modes imposed by ultrasmall dimensions in a submicron laser cavity. This method can rapidly probe the morphology and biochemistry of an organelle in a near-physiologic state. Thus, nanolaser spectroscopy is an ideal tool for studying the physical and biochemical changes in bioparticles.

The studies show that stressed or diseased states of the organelles can be quantified by the nanolaser spectra. The data revealed large changes in the physical optics of yeast mitochondria induced by genetic manipulation. These features reflect new states of stressed or diseased cells that are caused by large depletions or changes in biomolecular composition that contribute to the intrinsic refractive index. Most of these biomolecules are proteins with metallic complexes intended for normal electron transport function. The altered index is a biophysical consequence of dramatic changes that occur in the biomolecular distribution and subcellular organization of healthy cells under stress, or in disease states that produce cellular dysfunction. The nanolaser was successful in quantifying the biophysical statistics in this controlled experiment with genetic manipulation of the yeast mitochondria, and has been shown useful for studying other kinds of mitochondria.

Operation in the Rayleigh Limit

In the Rayleigh limit, a>>λ the particles scatter light over wide angles and do not support a longitudinal cavity mode. Instead, the particle and its motion produce a scattering or absorption loss or phase change and can randomly modulate a pre-existing laser mode defined by the cavity. The degree of modulation and its corresponding frequency spectrum will be dependent on the volume of the cavity mode, and the size, motion, and concentration of the particles. Larger particles will be expected to scatter more light and perturb the lasing mode more strongly. As the particle diameter decreases relative to the mode volume, the perturbation will decrease below a sensitivity limit defined by pre-existing noise in the mode volume. Sensitivity can be enhanced by operating a pre-existing cavity mode just above the lasing threshold condition. For example, intensity fluctuations can be recorded as a function of time, frequency, or angle to give information about the diffusional and rotational motion of bioparticles. This method has the advantage of being a non-destructive technique that can capture important information regarding size, motion, and dynamic interactions of the bioparticles with other bioparticles or material surfaces.

The light signal emitted from the cavity can be the direct beam of coherent light, coherent light scattered out the beam, or fluorescence from a fluorescent bioparticle. These methods have certain advantages over prior art methods of dynamic light scattering (DLS) and fluorescence correlation spectroscopy (FCS), and these two techniques are also adaptable to a resonant optical cavity and incorporated into the invention. FCS is a common technique to experimentally characterize fluorescent species (proteins, biomolecules, etc.) and their dynamics. Using confocal or two photon microscopy, light is focused on a sample and the measured fluorescence intensity fluctuations (due to diffusion, chemical reactions, aggregation, etc.) are analyzed using the temporal autocorrelation. FCS obtains quantitative information such as diffusion coefficients, hydrodynamic radii, average concentrations kinetic chemical reaction rates. DLS is used to determine the size distribution profile of small particles in solution. Time-dependent fluctuations in the scattering intensity are due to small molecules in solutions undergoing Brownian motion and dynamically changing coherent interference. The intensity fluctuation contains information about movement of the scatterers. The dynamic information of the particles is derived from an autocorrelation function g given by $$g^2(q, \tau) = \frac{\langle I(t)I(t+\tau)\rangle}{\langle I\rangle^2} \qquad (16)$$

where q is a wave vector, T is a delay time, and I is the intensity.

Both of these techniques are useful for gaining insight into bioparticle dynamics. However, DLS is limited by requirements for high purity specimens, ultra-clean surfaces of the liquid cuvette, and typically requires a large scattering volume ~10-100 uL. Thus, the measurement in a large volume gives only averages over large numbers of vesicles. FCS can sample very small volumes ~1 fL and probe single molecules. Unfortunately, the small volume implies high laser irradiance and consequent bleaching of the fluorescent probe molecules, limiting the FCS method.

The invention solves these technical difficulties by using coherent light fluctuations from intracavity scattering losses and absorption induced by the bioparticles. Either fluctuations in the coherent emitted beam or fluctuations in the coherent scattered light may be used. The dynamic motion of bioparticles can be studied by placing them into resonant optical cavities with micron and submicron dimensions formed with dielectric and/or semiconductor materials that have been surface-functionalized (e.g. polyethylene gycol) for optimal chemical, mechanical, and optical properties. The small lateral dimension and the standing wave electromagnetic field in the cavity creates a much smaller optical interaction volume than prior art, enhancing sensitivity. The cavities may take the form of a micro-titer plate (microcavity wells) with a static fluid or a microchannel cavity for flowing fluids.

The laser fluctuations can also be used to measure bioparticle motion in whole cells in the cavity. The fluctuations are sensitive to scattering from the distribution and motion of protein molecules and organelles in the cell. The method has the potential to probe intra-molecular polarization, molecular weight, shape and folding configuration structure since the coherent spectral linewidth is the Fourier transform of the time-correlated intensity fluctuations induced by molecular structure and motion.

None of the prior art on biological microcavity lasers teaches limitations to laser operation with small bioparticles. It doesn't teach the ultimate limits on bioparticle size to prevent laser operation. It doesn't teach limiting values on the particle refractive index, mismatch of index with carrier fluid, or particle size that would prevent the laser from working. Thus, prior art doesn't teach how the laser must be operated in a radically new way to measure very small bioparticles.

The ultimate limits of detectability for various bioparticles using optical techniques are influenced by light scattering. The total scattering cross section $\sigma_T$ of a single bioparticle scales as $((n^2-1)/(n^2+2))$ where $n=n_2/n_1$ is the ratio of the refractive index of the bioparticle to that of the surrounding media. For large values of n>10 (metallic behavior) this factor approaches a limiting value of 1. For small index differences $\delta=(n_2-n_1)/n$ the factor has the limiting form $4\delta^2/9$. The cross section also depends on the parameter $q=2\pi a/\lambda$ where a is the particle radius and λ the wavelength of light. At small q<<1, the cross section increases as $q^4$. At intermediate q>0.1 the dependence is stronger approximately ~$q^6$ in this case. For q≈0.5, the dependence becomes linear as q, and $\sigma_T$ becomes maximum at q≈1. For higher values of q, $\sigma_T$ exhibits damped oscillation and approaches twice the classical value of the cross section $\sigma=2\pi a^2$.

FIG. 10*a* shows a laser with a gain region 32, a resonant cavity 28 to confine light and select coherent light wavelengths, a means to extract light from the cavity. In the laser, a semiconductor provides the light, gain, and one reflective side of the cavity, and the glass chip completes the cavity and provides a partially transmissive mirror to leak light to the outside. The normal lasing process works as follows. The semiconductor wafer is energized externally with a separate pump laser or electrical pump to control spatial location and magnitude of the gain. The pump generates spontaneous (incoherent) light from a thin quantum-electronic layer in the semiconductor. In this condition below lasing threshold, the laser emits only incoherent, weak, spectrally broad light. As the pump power input is increased, a threshold is exceeded and the laser is triggered and the output power increases rapidly.

Figure 10B:
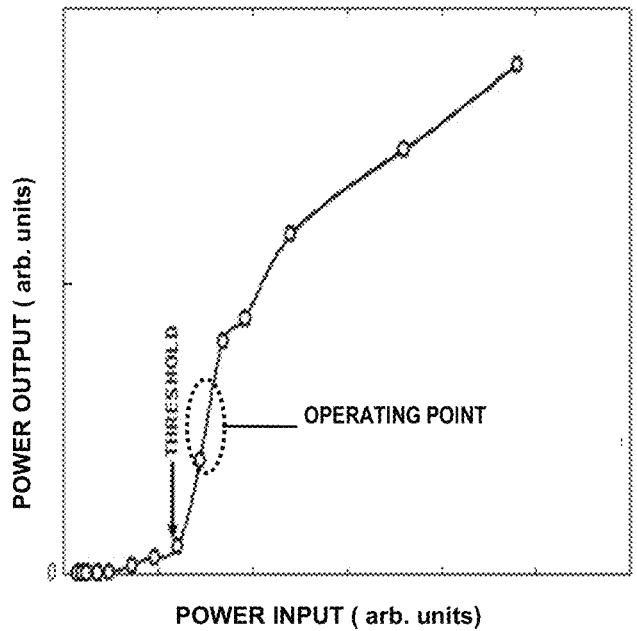
FIGS. 10a and 10b show a nanolaser for measuring properties of very small bioparticles.
Figure 10A:
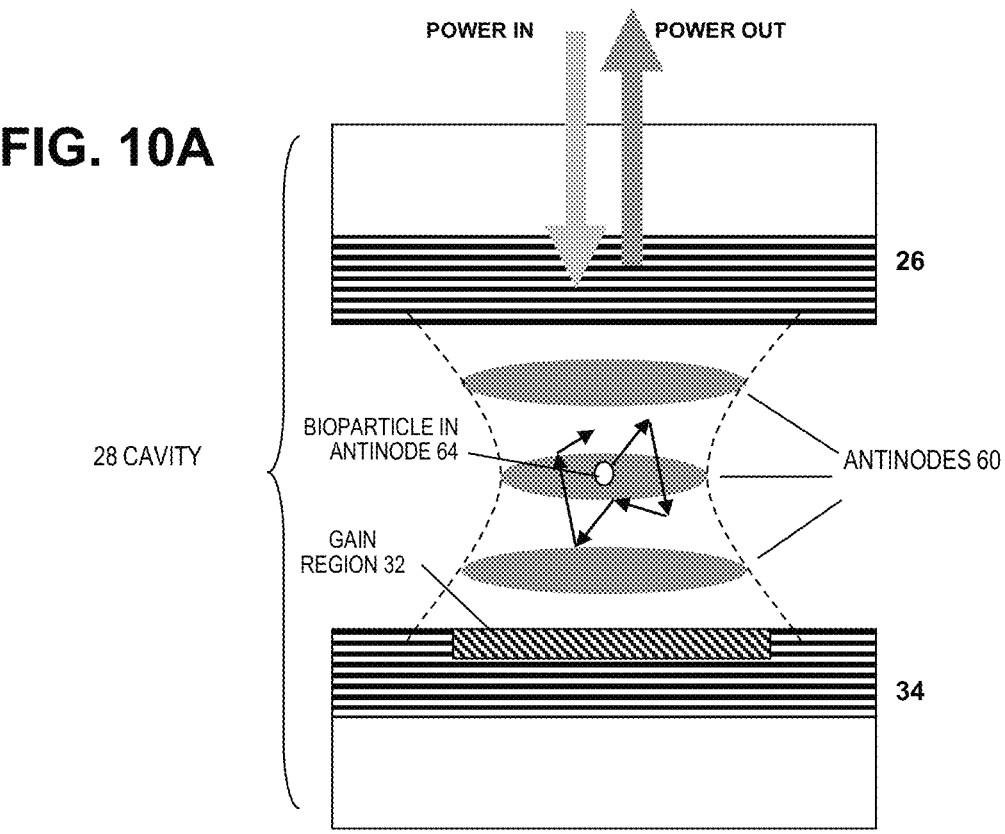
Figure 11A:
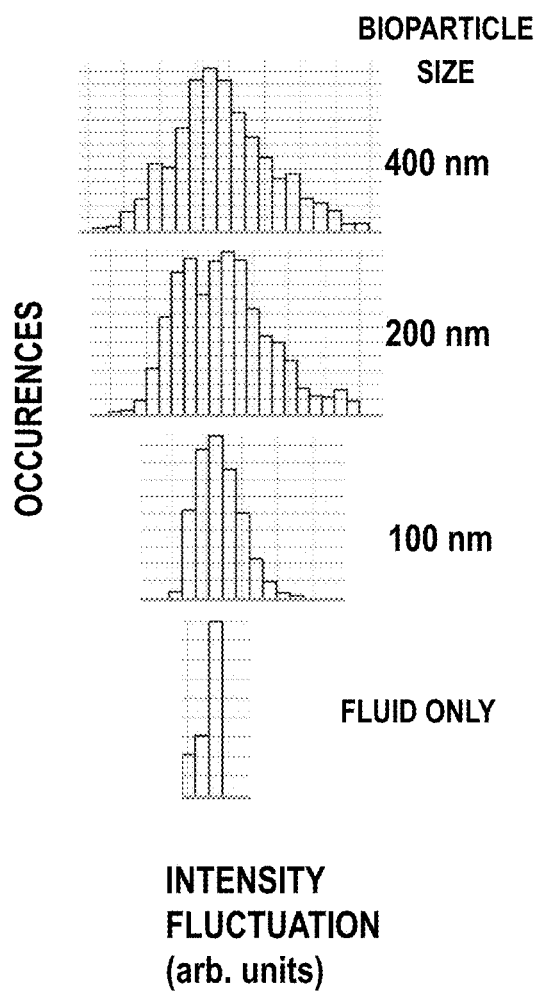
FIGS. 11a, 11b, and 11c show a method for measuring properties of very small bioparticles.
Figure 11B:
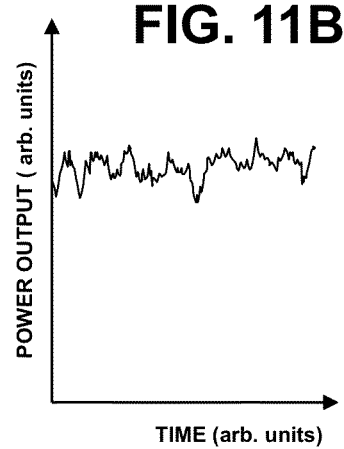
Figure 11C:
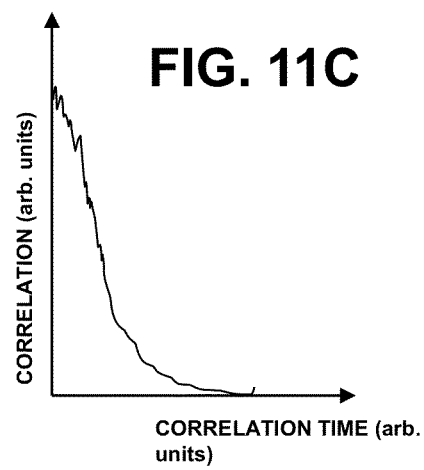
Figure 12:
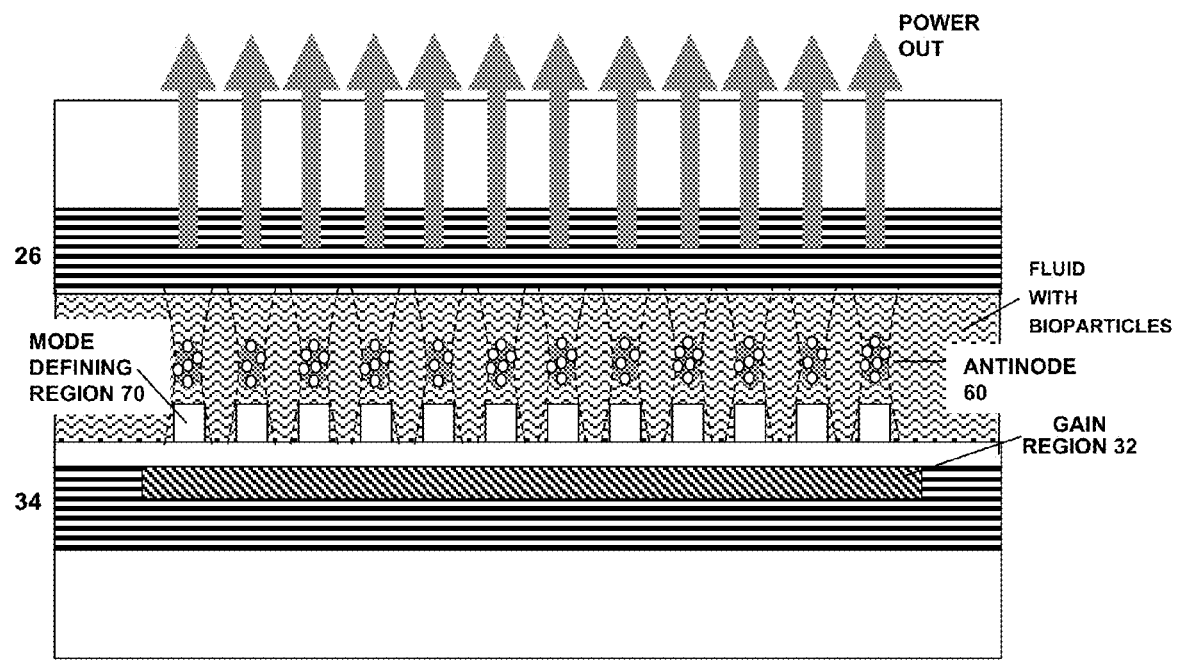
FIG. 12 shows a method for simultaneously detecting, analyzing, and manipulating bioparticles using intracavity resonant wave optical trapping.

FIG. 10b. shows a power output versus power input curve, showing that the light grows very rapidly (about 100-fold) and exhibits a highly nonlinear amplifying region. In this nonlinear region, a small change in the cavity can produce a large change in the output power. When bioparticles are present, they introduce scattering losses and phase change and effectively increase the threshold condition for lasing.

Figure 14A:
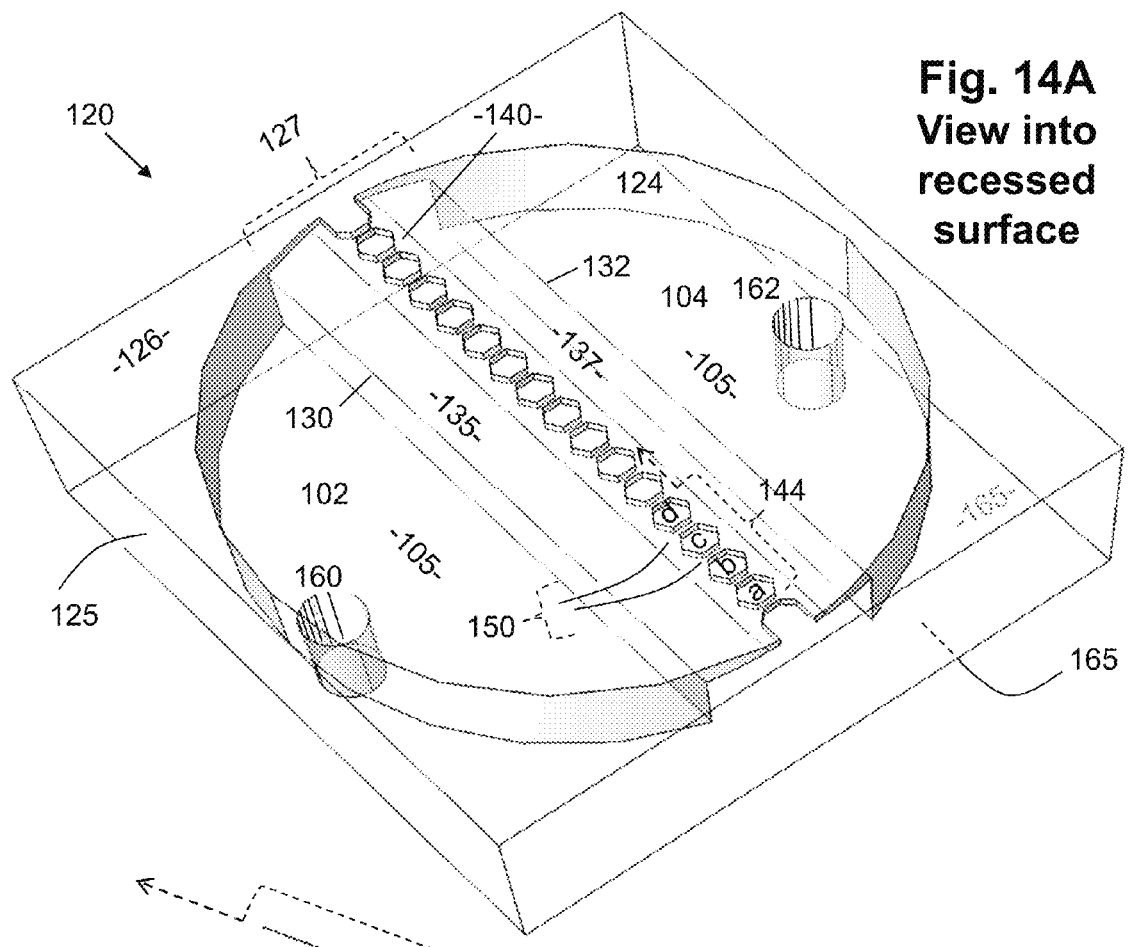
FIG. 14a shows a transparent perspective view of a microfluidic chip for enabling fluid transport into an optical cavity.

When the laser cavity length is the order of the wavelength of light, the laser operates on a single longitudinal and single transverse mode (single frequency). The cavity length can be shortened more to give a small number of field antinodes 60 (as shown in FIG. 10*a*) or single antinode to reduce the laser mode volume. The lateral mode dimension is reduced by fabricating a small lateral gain region or using a post waveguide or the like or using current confinement such as oxide confinement or ion implantation (electrical pump) or small pump spot or nonlinear (multiphoton) optical pumping.

When the mode volume is very small, the effect of individual bioparticles is more pronounced. The number of bioparticles in the lasing volume obeys Poisson statistics given by Eq. 5. The fluctuating number of bioparticles (64, FIG. 10*a*) in the mode volume is driven by Brownian motion and results in fluctuations in the lasing threshold condition. These fluctuations result in power output fluctuations (FIG. 11*b*) that can be compiled into histograms as in FIG. 11*a* or correlated in time to give correlation curves as shown in FIG. 11*c*. The laser signal can be self-correlated or cross-correlated with the pump source or light from another reference region in the laser. The shape of the correlation spectra gives information about the particle size and possible distribution of sizes.

Intracavity correlation spectroscopy can also be used to measure laser linewidth fluctuations arising from nanoparticles in the lasing mode volume. The coherent spectral linewidth is a measure of spatial correlation through a structure factor. For a laser microcavity of length L loaded with scattering centers having total scattering cross section $\sigma_T$ and average density $\rho$, the lasing linewidth $\delta\lambda$ in the high scatter limit is estimated by $\delta\lambda \approx (2/\pi)(K/P)(\rho L \sigma_T)^2$ where K is a linewidth enhancement factor, and P is the photon emission rate. Thus, the laser linewidth is sensitive to the scattering of light by bioparticles by a second order dependence on the scattering cross section. Increased scattering by correlation of bioparticles or interaction with other bioparticles will be evident by broadened lasing linewidth. In the event that chemical reactions occur between bioparticle species, the bioparticle can increase in size and change refractive index thus changing the scattering cross section and linewidth. The changes arising from interactions with multiple bioparticle species can be referenced to measurements on solutions with single species of bioparticles.

In the laser cavity a periodic electromagnetic field is set up in a standing wave. The field intensities at the antinodes are much higher (~100 times or more) than the external field intensity, giving larger scattering intensity. For small bioparticles undergoing Brownian motion, there will exist a 3-dimensional velocity distribution that interacts with the longitudinal periodic field. Scattering of light will occur only near the antinodes of the field, making the scattering volume smaller than the physical volume of the laser cavity mode. In addition, the field will exert optical-field gradient forces on the bioparticles. The force is a function of the intracavity field strength, bioparticle size and shape, polarizability, relative refractive indices of the fluid and bioparticle (dependent in turn on the molecular (e.g. chromophore) content in the bulk and surface or membrane). As a result, the bioparticles with lower velocities will tend to be confined in 2-dimensional oblate ellipsoids established by the longitudinal standing wave. This will tend to enhance the interaction within the longitudinal mode. As the intracavity field intensity is reduced, the bioparticles will exhibit more 3-dimensional motion. The differences between 2- and 3-dimensional motion will depend upon the detailed shape of the vesicles.

The dynamical interaction of the bioparticles within the cavity can be examined by varying the laser pump power, effects of internal or external optical trapping, light input versus light curves (threshold, maximum slope, and saturation level). Also, the bioparticles will be polarized by the electromagnetic field in the cavity. The polarization of the bioparticle will depend upon the frequency, shape, and polarizability. The polarization will influence the electromagnetic force exerted by the field on the bioparticle. Bioparticles with different shapes, such as rods or spheres, will exhibit different motion.

The bioparticles act as driven masses in a viscous medium and exhibit resonance motion under certain conditions. By changing the intracavity power, viscosity, electromagnetic field distribution, these conditions can be changed to drive the bioparticles into and out of resonance and determine their physical properties. The pump laser pulse frequency, pump laser pulse width (femtosecond, nanosecond, or continuous-wave) can be used to modulate the interaction of the field with the bioparticles to control and measure dynamical motion.

Multiple or arrays of lasing elements can be formed by defining waveguiding or gain guiding regions (32 with 70) as shown in FIG. 12. Such arrays can operate with independent elements or coupled lasers by changing their spacing. The array can serve to detect and analyze local interactions over a larger volume of bioparticles or generate a stronger signal. Further, the array antinodes 60 can serve to selectively trap bioparticles by controlling the pump power, frequency, or pump pulse duration. Simultaneously, the emitted light signals can provide information about the type of bioparticle held in the trap. Some bioparticles will respond to higher frequencies and will be trapped while others are not. Using controlled fluid flow, the untrapped bioparticles may be separated from the trapped bioparticles.

Finally, FIG. 13 shows how the array of light sources 80, operated as intracavity or extracavity lasers or spontaneous emitters, can be integrated with a reflector/detector array 84. Protective, biocompatible overlayers 82 are used to contact and enclose one or more living cells 86 in tissue culture. The nanolaser array is powered electrically or optically by a power interface 88. The output light output through a reflector to a detector array 84 to sense individual laser output intensities. The whole assembly acts as a self-contained biological probe system that eliminates the need for a microscope and associated optics. The system can be used to probe intracellular molecular activity, intercellular cell signaling, or extracellular molecular activity. These methods represent advantageous new ways to perform analyses of bioparticles and have wide ranging application for basic cell biology, cell culture, detection of disease, pathology, genetic engineering, environmental screening of toxins, pharmaceuticals, agricultural, and fermentation processes, biofuel production, and the like.

Fluid Transport Chip

It is also an object of this invention to use the optical cavity to rapidly isolate, spatially locate and probe individual particles by light interaction to provide statistical information of optical properties of a large population of particles. These processes are aided by a microfluidic transport chip fabricated as a component of the optical cavity. A best mode embodiment of the chip is shown in the transparent perspective drawing of FIGS. 14a and 14b. FIG. 14a shows a fluid transport chip 120 comprising a material substrate 125 having a first surface 126 fabricated with a pair of recessed reservoirs 102 and 104 with substantially vertical sidewalls 124 extending deep into the substrate to a substantially flat bottom surface —105- and separated by a barrier 127 extending less deep from the first surface 126. The barrier is fabricated with substantially vertical sidewalls 130 and 132 and a top horizontal surface 140 recessed less deeply than reservoirs 102 and 104. The barrier may have graded surfaces 135 and 137. The barrier is further patterned as in FIG. 14b into a fluid grate structure 144 with flow guides 144a,b,c,d . . . and channels 150 extending from the first surface 126 to the top barrier surface 140. The grate formed by the guides and shallow channels 150 interconnect said reservoirs 102 and 104. The barrier and grate serve to constrict flow from the reservoirs into the smaller grate openings or channels. Separate openings 160 and 162 extend from a reservoir surface (in the FIG. 14 the bottom surface of reservoir 102 and 104, respectively) through a surface of the chip 165 for transferring fluid between each reservoir and the exterior of the chip.

Figure 14B:
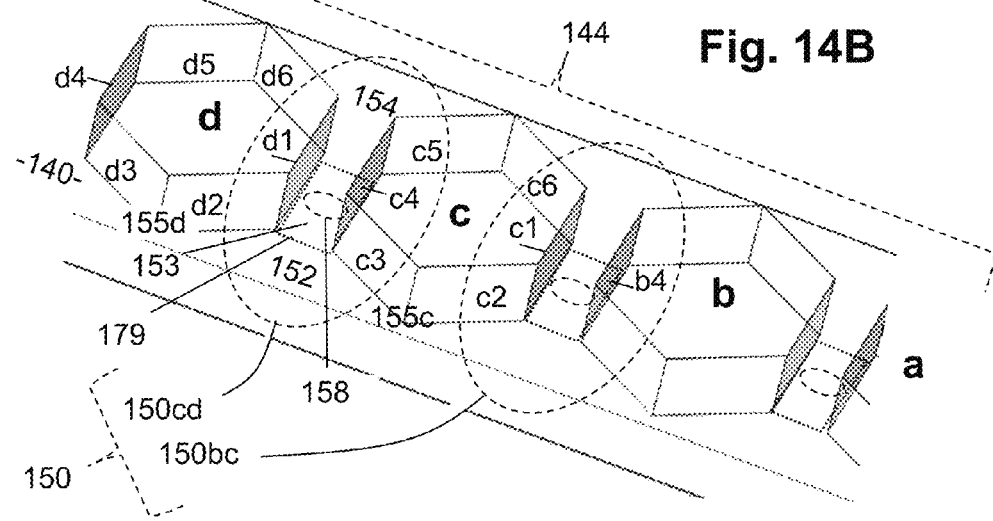
FIG. 14b shows a blowup perspective view of the flow guides and channels in a microfluidic chip.

The channels of the grate 144 are formed between guides 144a,b,c,d . . . that are shaped like a double prow, or hexagons as in FIG. 14b. A mouth 152 of a channel 153 is formed between the apex 155 of adjacent guides 155c and 155d. The apex serves to divert fluid laterally into the channel to constrict the flow along the barrier 127. Each channel has a cross-sectional area on the same order of magnitude as the cross-sectional area of the largest particle in the fluid, the volume of each reservoir being much greater than the volume of all channels. A first reflective surface layer 179 is on the top barrier surface 140 on the portion of the channels 153 extending into the substrate furthest from the first surface 126. (In practice, the entire chip surface is coated with reflective layers.) In the channel is an analysis region 158 of size D* defined by a laser pump spot, other light source, or diode light source. The chip substrate 125 is formed of a material transparent to light emitted by the optical cavity described hereafter.

An assembled fluidic optical cavity 121 containing flowing fluid (cross hatching) and particles (open circles) is shown in FIGS. 15a (top view through inverted fluidic chip) and 15b (cross sectional view of 15a). Said cavity is formed between the highly reflective surface layer 179 on channel surface 140 and a cover 170 for the channels having an inner surface 175 in fluid tight contact with the first surface 126 of the chip, and a second reflective surface layer 178, wherein the first and second reflective surface layers define the upper and lower boundaries of an optical cavity including the channels. A cover 170, which in the first embodiment includes an active structure 172 that includes a substrate 174, a plurality of semiconductor layers 178 forming a reflective surface, and a plurality of semiconductor layers 172 forming an active semiconductor that generates and amplifies light. The active structure 172 comprises at least one element selected from the group of an optically pumped semiconductor region, an electrically driven semiconductor diode, a light-emitting photonic nanostructure such as a photonic lattice, a triangular lattice, and a fluorescent material.

Glass chip 125 and cover 170 are in intimate physical contact such that optical fringes can be observed (defined as optical contact). An optical microscope is used to confirm that the contacted surfaces are no more than a few tens of nanometers apart. Because the interfacial seal is not perfect, some fluid may leak to the outside of the assembled cavity 121 to the exterior of the chip. To inhibit micro capillary action from wetting of the exterior perimeter of the chip interface, a guard ring groove 164 is etched the order of a millimeter into the chip 120. In another embodiment, the guard ring serves as an O-ring seal with a deformable ring material like rubber or other polymer known to those skilled in the art. External mechanical pressure is applied to the cavity 121 to maintain a good fluidic seal at the interface 141.

The surface 140 of channels 150 furthest from active structure 172 has a reflective coating 179 and, with reflective layer 178, forms a Fabry-Perot cavity that lases in the presence of a bioparticle 112 and provides a light output 114 indicative of the condition of the particle in channel 153. Because chip substrate 125 is transparent to the light generated by the device, the output 114 may be analyzed outside the chip with a spectrometer or other optical instrument (such as 46 and 50 shown in FIGS. 4, 7, and 9). The cavity reflectors can be dichroic to allow light of different wavelengths to pass in and out of the cavity. Thus, an external laser 173 (either above or below the cavity as in the figure) may be used to optically pump semiconductor 172. Or, the active structure 172 may be excluded and the external laser 173 (above or below the cavity) may be used to establish an optical resonance in a passive optical cavity. A more detailed explanation of the semiconductor structure and associated optics that may be used in the practice of the invention is provided in U.S. Pat. No. 5,793,485 and is incorporated herein by reference.

The improvement of this invention over the aforementioned patent resides in the structure which permits fluid under test to flow through the biocavity. Chip 120 may be formed from a block 125 of any material that is capable of being formed into the structure described herein and is transparent to the light emitted by the device. Glass was used for the described embodiment, but plastic, semiconductors, polymers and combinations thereof are examples of other such materials which could be used for chip 120.

Fluid input to the fluidic device 121 may be from a fluidic source container (36 in FIGS. 4, 7, and 9) through tubing to input holes 161,160 to the reservoir 102 and output through similar holes 162, 163 through tubing to a pump 38 and to an fluid collection container (40 in FIGS. 4, 7, and 9). These holes may extend from any part of the reservoir through any part of the chip, so long as they do not interfere with the channels 150 and the optical path extending from the cavity to the output light 114. For example, the axes of ingress and egress portal holes 161 and 160 may be offset to introduce a vortex motion to aid in mixing fluid elements in the cavity.

In the disclosed embodiment illustrated in FIGS. 4,7, and 9, a vacuum pump 38 is used to pull fluid under test from a supply source 36 through and input tube, cavity 28, output tube, and fluid collection vial 40. Alternately, the fluid could be driven by pressure, gravity feed, thermal effects, on-chip micromechanical motors, electrokinetic forces, surface tension forces, or other molecular-level forces. Instrumentation such as a video camera 50 and spectrometer 44/46 are used to interpret the output light signal and the flow of fluid through a transparent flowchip 125. Isolation vial 40 is provided with a stopper (not shown) through which the tubes pass from flowchip and to pump 38 in a manner well known in the art.

Operation of the Fluid Transport Chip

The average velocity v across any flow cross section A in a fluidic system is defined by the equation, $v=Q/A=1/A \iint v \cdot dA$ where Q is volume flow rate and v is the local velocity vector and dA the differential cross section element. When the cross sectional area of the reservoirs $A_1$ is much larger than the total cross section $NA_2$ of all N channels have identical cross section area $A_2$, the external pressure applied to the entire fluidic cavity to drive fluid through the entrance 160 and exit 162 ports is dropped almost entirely across the channels. This can be accomplished by making the total channel cross section about 100 or more times smaller (but not limited to this range) than the cross section of the reservoirs.

For a pressure applied across a channel In a simple 2-dimension geometry, the equation of motion can be solved (Hagen-Poiseuille equation) for a viscous fluid in laminar flow with non-slip boundary conditions giving the average flow velocity in a long channel of arbitrary cross section, $$v = \Delta p \, r_h^2 / 2L\eta, \quad (17)$$

where $\Delta p$ is the externally applied pressure difference across the channel, $r_h$ is the hydraulic radius given by A/P (channel cross sectional area A divided by perimeter P), L is the channel length, and n is the viscosity of the fluid. For a circular cross section $r_h = D/4$ where D is the diameter. For a rectangular cross section $r_h = wd/2(w+d)$ where w and d are the width and depth, respectively. This reduces to $r_h = w/4$ for a square and $r_h = d/2$ for a wide and shallow rectangle. For water through a shallow rectangular channel, equation 17 can be evaluated as $v \approx (100 \text{ cm/s})(\Delta p/14.7 \text{ psi}) \times (A/L \text{ in } \mu m))$. The volume flow rate is constant at every point in the incompressible fluid circuit and given by Q=vA. Alternately, the flow rate can be written as $Q = \Delta p G$ where G is a hydraulic conductance. The conductance is $G = (\frac{1}{2}L\eta)(\pi/4)(D^4/16)$ for a circular cross section, $G = (\frac{1}{2}L\eta)(\pi/4)(w^4/16)$ for a square, and $G = (\frac{1}{2}L\eta)d^3w$ for a wide and shallow rectangle.

The maximum particle rate $R_m$ through an analysis region of diameter $D^*$ to attain single particle analysis condition is given by $R \leq QC$ where C is the critical concentration (one particle in the analysis region at a time, typically on the order of $10^8/cm^3$ for small particles (but not limited to this value). For shallow rectangular channels this is given by $$R_m = (\Delta p/8\eta)(d^2/LD^*) \quad (18)$$

so higher rates occur with deeper and shorter channels. However, the channel cross section must be maintained small enough that the total channel conductance remains about 100 times smaller than the reservoir conductance.

The fluidic optical cavity is intended to locate and measure a single cell flowing from reservoir 102 to reservoir 104. The description of this process is aided by structural diagrams in FIGS. 14 and 15 and calculated fluid velocities, described hereafter, shown in FIG. 16 and FIG. 17. As shown in FIGS. 16b and 17b, the fluid path between reservoirs is constrained vertically (perpendicular to surface 126) by the barrier 127 with surface 140 and the top cover 170. FIG. 17b shows the fluid velocity field, calculated by finite element methods, as the fluid flows over the barrier 127 and into a channel 153. The fluid velocity field in the top view of FIG. 16a shows how the fluid passing over the barrier is further constrained laterally (along the barrier direction) by a grated surface 144 with a plurality of identical spaced pillar-shaped guides 144 (a,b,c, d . . . ). The guides extend from surface 140 to the plane surface 126 of chip 120. The volume between any two guides 144c, 144d is a channel 153 through which fluid flows in the practice of this invention.

As shown in FIG. 14b, each of guides 144 (a,b,c,d . . . ) has a plurality of sidewalls d1-d6. (An assigned letter designates each guide in the Figures; i.e., side d1 is on guide 144d.) The guides are double-prow-shaped to funnel the fluid under test, and biopaticles carried by this fluid, from one reservoir to another. For the preferred embodiment, each guide in the grated surface 144, for example 144d, has a generally hexagonal cross section formed by opposing parallel sides d2 and d5, d3 and d6, and d1 and d4 extending from surface 140 to the first surface 126. The volume between opposing sides d1 and c4 forms a channel 150cd. The guides could be elongated or shortened along the flow direction to alter the hexagonal shape to make the channel longer or shorter. Reservoir 102 connects to the mouth 152 of channel 150cd faces sides c3 and d2. Reservoir 104 connects to exit 154 of channel 150cd and faces sides c5 and d6. Because the tangential distance between guides decreases as a particle passes through the mouth 152 to channel 150cd between sides c3 and d4, these pairs of guides funnel particles through the channel between the guides and substantially increase its speed. If a guide was formed as a rectangular block, with a substantially vertical side extending perpendicular to the fluid flow, upstream particles could come to rest against the guide and not flow through a channel, while downstream particles could get caught in an eddy at the end of the guide and also come to rest.

Finite element methods were used to solve the 3D Navier-Stokes equation for an incompressible fluid in a flow cell with non-slip boundaries and 3D geometry similar to that illustrated in FIGS. 14 and 15. In FIG. 16, the computed velocity field distributions across the lateral (top view FIG. 16a) and vertical (side view FIG. 16b) dimensions of the flow channel. In FIG. 16a the magnitude of the velocity is proportional to the velocity vector size (length and arrow head size). Thus, short vectors appear only as a small dash while large vectors appear as a full arrow. The top view in FIG. 16a shows that the calculated lateral velocity field vectors, in a horizontal plane centered in the channel, converge into the channel 181 as the fluid flows from left to right. A parabolic velocity profile 182 transverse to the flow develops in the channel 153, due to non-slip boundary conditions, and then the velocity vectors diverge 183 out of the right side of the channel. As shown by the length of the velocity vectors, the speed of the fluid in the channel 182 is much higher than the speed in the reservoirs 180.

This change in speed corresponds to an acceleration and can also be seen in the cross sectional drawing of 16b that shows the vertical velocity vector distributions (all vectors drawn as lines without arrow tips for clarity) at several points (left side of lines) along a central, vertical plane in the channel parallel to the flow direction. Near the left edge of the barrier 127 (which has no side gradings 135, 137 in this illustration) a parabolic velocity distribution 184 develops as the fluid approaches the channel. The maximum velocity distribution 185 develops just inside the channel at a position 186 about 1/10 of the channel length. The distribution at the center 189 is slightly lower, flatter, more uniform, and not strictly parabolic. It is surprising that the fluid speed does not reach its maximum at the channel center, but rather near the entrance 186 and at a position 187 and distribution 189 symmetrically located about the channel center 190 from position 186.

Figure 17A:
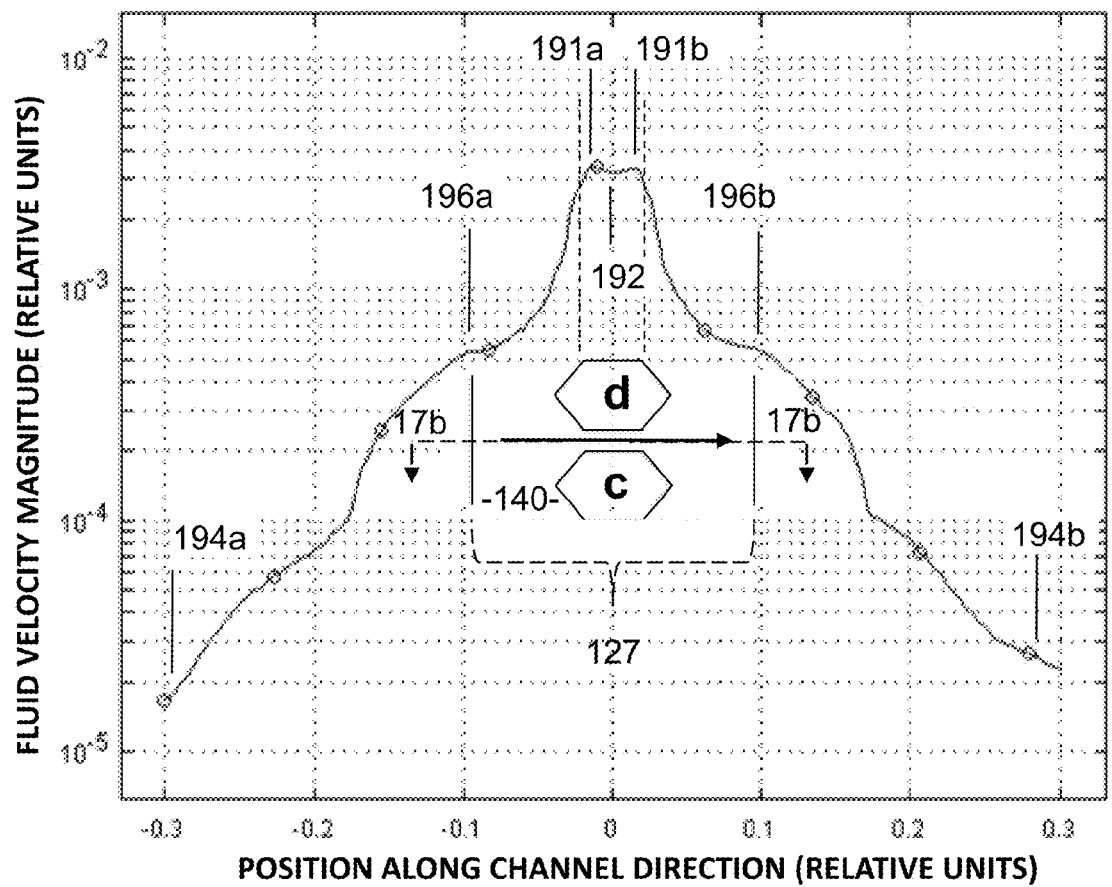
FIG. 17a shows the computed velocity of fluid flow along the direction of the channel as a function of channel position.
Figure 17B:
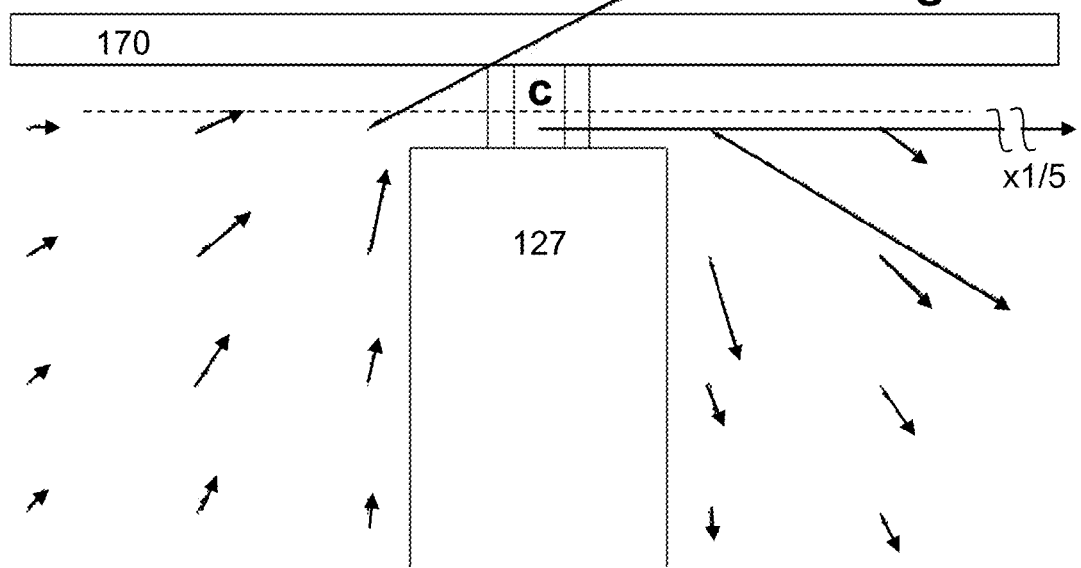
FIG. 17b shows a cross sectional view of the velocity distribution.

FIG. 17a shows a profile of the computed magnitude of the velocity vector along a line centered in the channel along the flow direction between guides c and d (illustrated in the inset figure). The profile extends from the reservoir to the barrier and across the channel to the other reservoir. The profile exhibits a central double peak (191a, 191b) with a shallow saddle 192 in the channel region. The profile has shoulders 196a and 196b associated with the barrier region and side wings 194a and 194b tapering to lower velocity in the reservoirs. The maximum velocity in the channel is about 100 times larger than that in the reservoirs (points 194a and 194b) and about 10 time larger than that near the barrier edges (points 196a and 196b). FIG. 17b is a cross sectional view of FIG. 17a showing the distribution of velocity vectors in a vertical plane containing the center of the channel. The vectors show the large acceleration that takes place as the fluid transfers up and over the barrier from the left reservoir and into the channel and then down into the right reservoir.

The higher velocity in the channel (typically in the range of one to a hundred centimeters per second, but not limited to this range) is a consequence of the equation of continuity div·v=0 for an incompressible fluid equation accelerating into a channel cross section much smaller (the order of $10^4$ times smaller but not limited to this value) than the reservoir cross section. The symbol div is the divergence operator and v is the velocity field vector. The fabricated channel volume is much smaller (on the order of a million times smaller but not limited to this value) than the reservoir volume. This condition has several important consequences. One, the small volume isolates an individual particle in the channel when the average particle density is one or less per channel volume. Two, the high fluid speed in the channel minimizes the time for binding interaction between a bioparticle and a channel surface. Three, the high speed jet of fluid (which may comprise a fluid intended for cleaning, priming, or wetting the channel separate from the particle fluid) through the channel helps polish and maintain clean optical surfaces. Four, the channel transit time (typically 1 to 100 microseconds, but not limited to this range) is still orders of magnitude slower than the interaction time of light (typically femtoseconds to nanoseconds, but not limited to this range) required to probe the particle's optical properties.

In FIG. 14b the optical probing of the particle typically takes place at selected points in the region of the top barrier 140 and especially within the channel area 153. In a preferred embodiment, the light probe emanates from a photo-pumped spot 158 of diameter D* in the active region 172 inside the channel area 153. Using a lens like 24 in FIG. 4 or 7, or 54 in FIGS. 7 and 9, the pump spot can be adjusted in size (lens focusing) or moved (lens lateral translation) to other spots within the channel area. The spot diameter D* is typically chosen to be much larger than the particle size and about ¼ to ½ (not limited to these values) the channel width along the center flow line of the channel 153 and the maximum in the lateral velocity distribution. Under these conditions the light sampled volume is less than about ¹/₁₀ of the channel volume. This smaller probe volume helps to further isolate and located individual particles. Thus, particle concentration can be as high a one particle per probe volume to ensure a high probability of sampling only one particle. As mentioned earlier, aggregated particles register as multiple laser frequencies so single particles can still be counted individually.

A preferred embodiment is to locate the pump spot in the very center region of the channel (158 in FIG. 16a) where the flow velocity is more uniform. Another preferred embodiment is to locate the pump spot nearer the entrance 186 and exit 187 of the channel center flow line where the fluid velocity is maximum. In other embodiments, the light source is an electrically driven junction diode fixed in the channel. In this embodiment the preferred location of the light source is at the center of each channel.

For large spot sizes, larger than the cavity depth, the electromagnetic modes are those of a planar cavity with a circular light emitter on one side as a boundary condition. The empty cavity modes can be approximated by 2D disk modes. In another preferred embodiment, the channel width between guides is made so small as to define additional optical confinement from parallel sidewalls such as 144d1 and 144c4 in the grated surface 144. The sidewalls can be uncoated or coated. In this case the electromagnetic modes of the cavity are substantially those of a 3D rectangular box. The position and spacing of the frequencies in the 2D and 3D cases can be used as reference frequencies to aid the measurement of the light frequency of the cavity in the presence of the particle.

Many other configurations of guides in the grated surface 144 are contemplated. As shown, the cross sectional area (as viewed from top a,b,c . . . of each guide is rectangular with pointed ends facing each reservoir. Alternatively, the cross sectional area could be an oval or an ellipse, or any other form that tends to funnel particles into the volume between guides. In addition, the dimensions of the guides are a matter of design dependent on factors such as how many guides are desired and the size of the channels. The cross sectional of the channels is generally rectangular in the disclosed embodiments, but they also could be other polygons or triangular or have curved surfaces.

Other embodiments of of the fluidic optical cavity 121 are contemplated in the practice of this invention. For example, the light emitting structure 172 could be a light emitting polymer. In addition, the active light emitting region could be limited to only that structure which is directly aligned with channels 150 or other multiple external lasers aligned with each channel. although other structure would have to seal the reservoirs. Furthermore, the junction between active structure 172 and chip 120 does not have to be planar. In addition, the reservoirs could be embedded in chip 20 and not sealed by cover 170.

An alternative embodiment includes a chip 120 as discussed above with a cover 170 that consists of a rigid material with a reflective layer 178 adjacent channels 150. There is no gain region incorporated into this cavity of this embodiment; an external laser 173 is used to pump a Fabry-Perot cavity defined by a channel 150 and reflective layers 179, 178. In one embodiment, the presence of particles in channels 150 will cause a frequency shift to the resonant frequency of the cavity, and light will be emitted that is detected. In another embodiment, the light from external laser 173 excites fluorescence in particles carried by the fluid which is amplified by the optical cavity to produce an output for a detector.

Other versions of this embodiment are also contemplated. For example, laser 173 could be on the same side of chip 120 as output 114, with suitable beam splitters and other dichroic optics utilized as known to those of ordinary skill in the art.

Chip 120 may be fabricated by many known techniques, such as wet or dry etching, plasma etching, etc. For one test of the invention, the channels and reservoirs of a glass chip 120 were wet etched with hydrofluoric acid (HF). After a thorough cleaning, a photoresist mask was applied, exposed, and developed to define areas to be protected. The chip was then etched in a 2:1 solution of HF and deionized water for seconds to minutes, depending on the desired depth of the etch. After etching, the photoresist was removed and the chips were then dried and profiled to determine the final etch depth. This process was done in two steps, with the reservoirs and channels being etched separated. Using only photoresist as a mask, etch depths in the range of 10 to 20 microns could be achieved before undercutting became severe.

Alternatively, reservoirs or guides on 144 could be formed by reactive ion etching, inductively coupled plasma etching, ion beam etching, laser ablation, cut with a laser or other device capable of making very small grooves in chip 120. Mechanical abrasion, particle blasting, or ultrasonic cutting are other options for fabricating features on the flow chip. The triangular channel referenced above could be formed by cutting parallel 'vee's in surface 126. In addition, while in the aforementioned embodiments channels 150 are cut from the chip, so guides on 144 are formed from and are integral parts of chip 120, guides on 144 could be formed by deposition of a similar or different material on surface 140.

The dimensions of experimentally fabricated channels 150 ranged in width from 10-50 µm, in depth from 0.1-25 µm, and in length from 90-500 µm. The number of channels in each chip ranged from 12-16. The range produces a difference of three orders of magnitude in the hydraulic conductance of the channels. These different channel dimensions allow for different cell sizes and velocities.

Although guides on 144 are shown with vertical sides, it should be understood that these sides could be tapered, with the area of the top surface being smaller than the opposing area at the bottom on surface 140. In addition, generally vertical sides may also taper inwardly if they are undercut by etchant. Furthermore, anywhere a substantially vertical surface intersects a substantially horizontal surface, the intersection is shown to be a 90° turn. These intersections may also be rounded by known manufacturing techniques.

SUMMARY

The invention described presents advantageous new ways to perform analyses of bioparticles and has wide-ranging application for small particle analysis, cell biology, detection of disease, pathology, environmental monitoring, pharmaceuticals, agriculture, and fermentation processes, biofuels, and the like.

What is claimed is:

1. An apparatus for analyzing a bioparticle in an optical cavity, said apparatus comprising:
   a light source to establish optical resonance and a standing wave in said optical cavity;
   a photodetector for detecting light emitted from the optical cavity;
   and the optical cavity comprising:
      a fluid transport chip having:
         a first surface;
         a pair of reservoirs spaced along said first surface, each reservoir recessed into said chip, and a means for transferring fluid among said reservoirs and the exterior of the chip;
         an area of the first surface between said reservoirs acting as a barrier between the reservoirs;
         an array of one or more channels recessed from the first surface into said barrier and connecting the reservoirs
         a first reflective surface on a portion of said channels furthest from the first surface, the chip adjacent to the channels being formed of a material transparent to said light emitted from the optical cavity;
      a cover for the channels having:
         an inner surface in fluid tight contact with the first surface of the chip;
         a second reflective surface, wherein said first and second reflective surfaces define the limits of the optical cavity including the channels; and
         an analysis region in the optical cavity.

2. The fluid transport chip of claim 1 wherein said fluid transport chip is formed of at least one material from the group consisting of glass, plastic, semiconductors, polymers, and materials transparent to light of some wavelengths between 200 and 1500 nm.

3. The fluid transport chip of claim 1 wherein said fluid transport chip is further provided with dichroic optical coatings for transmitting pump light wavelengths and reflecting intracavity light.

4. The channels of claim 1 wherein said channels comprise a grated surface in said barrier separating said reservoirs, said grated surface has said channels defined by a plurality of guides with openings substantially parallel to and recessed from said first surface and connecting said pair of reservoirs.

5. The channels of claim 4 wherein the fluid flow in said channels is constricted vertically by said barrier in combination with said cover and laterally by said grated surface comprising said guides with said parallel openings forming said channels.

6. The channels of claim 4 wherein a plurality of said barriers with said grated surface having grates of different dimensions for isolating said bioparticle of a certain size.

7. The cover of claim 1 wherein said cover is further integrated with a light source selected from at least one of the group consisting of a fluorescent material, a semiconductor region including said second reflective surface, a microcavity laser, a semiconductor laser diode, a semiconductor light-emitting diode, and an array of diodes aligned with said array of channels.

8. The cavity of claim 1 wherein said cavity further includes a gain region.

9. The cavity of claim 1 wherein said cavity is a Fabry-Perot cavity.

10. The analysis region of claim 1 wherein said analysis region is defined by at least one selected from the group of a pump laser spot on semiconductor material, a diode light source, a focus of an external laser, a region of a fluorescence material, and a gain region.

11. The cavity of claim 1 wherein said cavity further includes a material structure to define optical modes comprising at least one structure selected from the group consisting of a post, a post array, a triangular lattice of posts, a photonic lattice, and a waveguide.

12. The analysis region of claim 1 wherein said analysis region is located in at least one region selected from the group consisting of center of said channel, a saddlepoint in velocity distribution, a maximum in velocity distribution, an entrance region of said channels, and an exit region of said channels.

13. The cavity of 1 wherein said tight contact between the chip and cover uses a least one sealing method selected from the group of optical contact, intimate physical contact, surface tension, mechanical pressure, chemical, and o-ring.

14. The cavity of claim 1 wherein the inner surfaces of said cavity are further functionalized to control fluid flow.

15. The cavity of claim 1 wherein said reservoirs have hydraulic conductance 100 times or more higher than the combined hydraulic conductance of all channels.

16. The bioparticle of claim 1 wherein said bioparticle has average concentration of one or less bioparticle per said channel volume to isolate an individual bioparticle in said channel.

17. The cavity of claim 1 wherein a fluid velocity in said channels is adjusted by the external pressure and ratio of reservoir cross sectional area to total channel cross sectional area to control the transit time of said bioparticle across said channel to less than 100 microseconds.

18. The cavity of claim 1 wherein said fluid is a high speed jet of fluid without bioparticles comprising at least one fluid type selected from the group consisting of fluids intended for cleaning, priming, wetting, and coating with molecular layers the inner surfaces of said cavity.

19. The cavity of claim 1 wherein said reflective surfaces are structures comprising at least one structure selected from the group consisting of layers, waveguides, photonic lattices, periodic bandgap materials, and fibers, and said structures comprise at least one material selected from the group of dielectrics, metals, glasses, plastics, semiconductors, and polymers and said structures comprise at least one geometrical form selected from the group of planar, box-like, rod, cylindrical, ring, and spherical.

20. The cavity of claim 1 wherein said cavity comprises an intracavity fluid grate with at least one channel for flow of fluids.

21. The cavity of claim 1 wherein said reflective surfaces comprise parallel planar high reflectors facing each other.

22. The cavity of claim 1 wherein at least one approximate dimension of said cavity is selected from the group consisting of said analysis region, size of said bioparticle, the wavelength of said standing wave, and a dimension in the range 100 to 3000 nanometers.

23. The cavity of claim 1 wherein at least one surface of said cavity is provided with a layer to enhance said cavity properties including at least one property selected from the group consisting of biocompatible, optical, fluidic, mechanical and electrical.

24. The light source of claim 1 wherein at least one light source is selected from the group consisting of optical pumping and electrical injection.

25. The cavity of claim 1 wherein said cavity is includes at least one element selected from the group consisting of a semiconductor, a fluorescent material, a microcavity laser structure, a nanolaser, a photonic lattice, a photonic nanostructure, quantum dots, quantum arrays, quantum wires, and quantum layers.

26. The photodetector of claim 1 wherein said photodetector uses machine vision for detection and analysis of at least one measured property selected from the group consisting of, a spectrum, a wavelength, a linewidth, an intensity, a polarization, an image, a position, a size, a morphology, a refractive index, a polarizability, and a statistical property.

* * * * *